United States Patent
Parthasarathy et al.

(10) Patent No.: US 8,835,157 B2
(45) Date of Patent: Sep. 16, 2014

(54) SUPPORTED REAGENTS, METHODS, AND DEVICES

(75) Inventors: Ranjani V. Parthasarathy, Woodbury, MN (US); Michael E. Danielson, St. Paul, MN (US); John C. Faletti, Cottage Grove, MN (US); William Bedingham, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 722 days.

(21) Appl. No.: 12/597,410

(22) PCT Filed: Apr. 25, 2008

(86) PCT No.: PCT/US2008/061484
§ 371 (c)(1),
(2), (4) Date: Oct. 23, 2009

(87) PCT Pub. No.: WO2008/134462
PCT Pub. Date: Nov. 6, 2008

(65) Prior Publication Data
US 2010/0136554 A1    Jun. 3, 2010

(51) Int. Cl.
*C12M 1/00* (2006.01)
*C12M 1/34* (2006.01)
*C12Q 1/68* (2006.01)
*G01N 33/00* (2006.01)
*B01L 3/00* (2006.01)
*G01N 33/543* (2006.01)

(52) U.S. Cl.
CPC ........... *B01L 3/5027* (2013.01); *B01L 2200/12* (2013.01); *B01L 2200/16* (2013.01); *G01N 33/54366* (2013.01); *B01L 2300/0887* (2013.01); *B01L 2300/0864* (2013.01); *G01N 33/54393* (2013.01); *B01L 2300/0803* (2013.01)
USPC ...... 435/283.1; 435/6.1; 435/287.2; 422/68.1

(58) Field of Classification Search
CPC . B01L 3/5027; G01N 33/54366; C12M 1/34; C12Q 1/68
USPC ...................... 435/6.1, 283.1, 287.2; 422/68.1
See application file for complete search history.

(56) References Cited

U.S. PATENT DOCUMENTS 4,363,874 A   12/1982   Greenquist
4,528,159 A   7/1985   Liston
(Continued)

FOREIGN PATENT DOCUMENTS

WO   WO 96/34028   10/1996
WO   WO 96/34029   10/1996
(Continued)

OTHER PUBLICATIONS

"BAX System Q7, The Power to Do More," DuPont, E. I. DuPont de Nemours and Company, 21 pages (Copyright 2006).
(Continued)

*Primary Examiner* — Narayan Bhat

(57) ABSTRACT

Methods of providing at least one reagent for use in a device for processing sample material, delivering at least one reagent to a device for processing sample material, and adding at least one reagent to at least one of the steps in a process for detecting or assaying a nucleic acid; a support film coated with a dry reagent layer; and a device for processing sample material having a support film coated with a dry reagent layer contained within at least one chamber of the device are disclosed.

7 Claims, 3 Drawing Sheets

(56) References Cited

U.S. PATENT DOCUMENTS

| | | | |
|---|---|---|---|
| 4,654,267 A | 3/1987 | Ugelstad et al. | |
| 4,668,472 A | 5/1987 | Sakamoto et al. | |
| 4,820,627 A | 4/1989 | McGeehan | |
| 5,053,197 A | 10/1991 | Bowen | |
| 5,278,079 A | 1/1994 | Gubinski et al. | |
| 5,415,838 A | 5/1995 | Rieger et al. | |
| 5,461,134 A | 10/1995 | Leir et al. | |
| 5,556,771 A | 9/1996 | Shen et al. | |
| 5,948,673 A * | 9/1999 | Cottingham | 435/287.2 |
| 5,948,695 A * | 9/1999 | Douglas et al. | 436/518 |
| 6,007,914 A | 12/1999 | Joseph et al. | |
| 6,251,621 B1 * | 6/2001 | Lawrence et al. | 435/18 |
| 6,627,159 B1 | 9/2003 | Bedingham et al. | |
| 6,649,403 B1 | 11/2003 | McDevitt et al. | |
| 6,720,187 B2 | 4/2004 | Bedingham et al. | |
| 6,734,401 B2 | 5/2004 | Bedingham et al. | |
| 6,814,935 B2 | 11/2004 | Harms et al. | |
| 6,835,542 B2 | 12/2004 | Becker et al. | |
| 6,987,253 B2 | 1/2006 | Bedingham et al. | |
| 7,023,168 B1 | 4/2006 | Patel et al. | |
| 7,026,168 B2 | 4/2006 | Bedingham et al. | |
| 7,112,552 B2 | 9/2006 | Simpson et al. | |
| 7,164,107 B2 | 1/2007 | Bedingham et al. | |
| 7,192,560 B2 | 3/2007 | Parthasarathy et al. | |
| 7,309,588 B2 | 12/2007 | Burg et al. | |
| 7,322,254 B2 | 1/2008 | Bedingham et al. | |
| 7,435,381 B2 * | 10/2008 | Pugia et al. | 422/421 |
| 2002/0047003 A1 | 4/2002 | Bedingham et al. | |
| 2002/0048533 A1 | 4/2002 | Harms et al. | |
| 2002/0052050 A1 | 5/2002 | Douglas et al. | |
| 2002/0064885 A1 | 5/2002 | Bedingham et al. | |
| 2003/0138779 A1 | 7/2003 | Parthasarathy et al. | |
| 2004/0038388 A1 | 2/2004 | Yamamoto et al. | |
| 2004/0152076 A1 | 8/2004 | Wilson et al. | |
| 2004/0220498 A1 | 11/2004 | Li et al. | |
| 2004/0248087 A1 | 12/2004 | Burg et al. | |
| 2005/0118217 A1 | 6/2005 | Barnhart et al. | |
| 2005/0126312 A1 | 6/2005 | Bedingham et al. | |
| 2005/0129572 A1 * | 6/2005 | Schulman et al. | 422/56 |
| 2005/0129583 A1 | 6/2005 | Bedingham et al. | |
| 2005/0142571 A1 | 6/2005 | Parthasarathy et al. | |
| 2006/0088863 A1 | 4/2006 | Yamamoto et al. | |
| 2006/0134221 A1 | 6/2006 | Geall | |
| 2006/0134767 A1 | 6/2006 | Buser-Doepner et al. | |
| 2006/0194207 A1 * | 8/2006 | Mitani et al. | 435/6 |
| 2006/0257494 A1 | 11/2006 | Vachon et al. | |
| 2007/0009391 A1 | 1/2007 | Bedingham et al. | |
| 2007/0010007 A1 | 1/2007 | Aysta et al. | |
| 2007/0099222 A1 | 5/2007 | Gee et al. | |
| 2007/0184547 A1 | 8/2007 | Handique et al. | |
| 2008/0084186 A1 | 4/2008 | Elder et al. | |
| 2008/0149190 A1 | 6/2008 | Bedingham et al. | |
| 2010/0062421 A1 | 3/2010 | Xia et al. | |
| 2010/0136554 A1 | 6/2010 | Parthasarathy et al. | |

FOREIGN PATENT DOCUMENTS

| | | |
|---|---|---|
| WO | WO 96/35458 | 11/1996 |
| WO | WO 00/68336 | 11/2000 |
| WO | WO 02/46398 | 6/2002 |
| WO | WO 02/082086 | 10/2002 |
| WO | WO 03/035386 | 5/2003 |
| WO | WO 2004/057331 A1 | 7/2004 |
| WO | WO 2005/040228 | 10/2004 |
| WO | WO 2005/061084 | 7/2005 |
| WO | WO 2005/068628 | 7/2005 |
| WO | WO 2006/119280 | 11/2006 |
| WO | WO 2007/016633 A1 | 2/2007 |
| WO | WO 2007/085043 | 8/2007 |
| WO | WO 2009/061864 | 5/2009 |

OTHER PUBLICATIONS

"Silicone Pressure Sensitive Adhesives", *Handbook of Pressure Sensitive Adhesive Technology*, $3^{rd}$ Edition, pp. 508-517.

BAX System Q7 Brochure, E. I. DuPont de Nemours and Company, Copyright 2006, 17 pages.

Fig. 8-16 on p. 173 of *Handbook of Pressure Sensitive Adhesive Technology*, Donatas Satas (Ed.), 3rd Edition, Van Nostrand Rheinhold, New York, 1989).

*Handbook of Pressure Sensitive Adhesive Technology*, Donatas Satas (Ed.), $2^{nd}$ Edition, p. 172, Van Nostrand Reinhold, New York, NY, 1989.

Hydration Pressure of a Homologous Series of Nonionic Alkyl Hydroxyoligo(ethylene oxide) Surfactants; Pfeiffer et al.; Phys. Chem. Chem. Phys., 2004, 6, pp. 614-618.

International Search Report of PCT/US08/061490 Aug. 18, 2008; 4 pages.

International Search Report of PCT/US08/82543 Apr. 14, 2009, 5 pages.

International Search Report of PCT/US2008/061484 Aug. 12, 2008; 4 pages.

U.S. Appl. No. 60/985,933, Menon et al. "Processing Device Tablet," filed Nov. 6, 2007.

U.S. Appl. No. 60/913,812, Xia et al., "Compositions, Methods, and Devices for Isolating Biological Materials," filed Apr. 25, 2007.

U.S. Appl. No. 60/985,827 Bedingham, "Chemical Component and Processing Device Assembly," filed Nov. 6, 2007.

Fig. 8-16 on p. 173 of *Handbook of Pressure Sensitive Adhesive Technology*, Donatas Satas (Ed.), $2^{nd}$ Edition, Van Nostrand Rheinhold, New York, 1989).

U.S. Appl. No. 60/913,812, titled Compositions, Methods, and Devices for Isolating Biological Materials, filed on even date herewith.

International Publication No. WO 96/35458 (and its related U.S. Appl. Nos. 08/427,788 (filed Apr. 25, 1995); 08/428,934 (filed Apr. 25, 1995); 08/588,157 (filed Jan. 17, 1996); and 08/588,159 (filed Jan. 17, 1996).

International Publication No. WO 96/34028 (and its related U.S. Appl. Nos. 08/428,299 (filed Apr. 25, 1995); 08/428,936 (filed Apr. 25, 1995); 08/569,909 (filed Dec. 8, 1995); and 08/569,877 (filed Dec. 8, 1995)).

International Publication No. WO 96/34029 (and its related U.S. Appl. Nos. 08/428,735 (filed Apr. 25, 1995) and 08/591,205 (filed Jan. 17, 1996)).

* cited by examiner

SUPPORTED REAGENTS, METHODS, AND DEVICES

CROSS REFERENCE TO RELATED APPLICATIONS

This application is the National Stage filing under 35 U.S.C. 371 of International Application No. PCT/US2008/061484, filed Apr. 25, 2008, which claims the benefit of U.S. Provisional Application No. 60/913,814, filed Apr. 25, 2007, which is incorporated herein by reference in its entirety.

BACKGROUND

Biological reagents associated with nucleic acid manipulation techniques can be expensive and subject to degradation during preparation, storage, and/or use. Nucleic acid manipulation techniques include, for example, amplification methods such as polymerase chain reaction (PCR); target polynucleotide amplification methods such as self-sustained sequence replication (3SR) and strand-displacement amplification (SDA); methods based on amplification of a signal attached to the target polynucleotide, such as "branched chain" DNA amplification; methods based on amplification of probe DNA, such as ligase chain reaction (LCR) and QB replicase amplification (QBR); transcription-based methods, such as ligation activated transcription (LAT), nucleic acid sequence-based amplification (NASBA), amplification under the trade name INVADER, and transcriptionally mediated amplification (TMA); and various other amplification methods, such as repair chain reaction (RCR) and cycling probe reaction (CPR). Biological reagents such as enzymes, primers, and probes are used in nucleic acid amplification and detection.

Typically, biological reagents, such as enzymes, are stored in a glycerol solution at −20° C. or in a dried form to increase storage stability. Examples of dried forms include powders, spheres, tablets, and thin glassy films. However, powders can be difficult to measure, freeze-dried structures such as spheres are fragile and tend to disintegrate when handled, and tablets and thin glassy films can be slow to dissolve.

Even though several formats have been considered for storing and providing biological reagents, a continuing need exists for biological reagent formats that can be readily manufactured, stored, and used.

SUMMARY OF THE INVENTION

The present invention provides a support film coated with a reagent layer, methods involving providing and using a support film coated with a reagent layer, and a device, which includes a support film coated with a reagent layer. The support film imparts dimensional stability and toughness to the reagent layer without substantially interfering with the function of the reagent(s) in the reagent layer. The reagent can, thereby, be provided with a minimal amount of associated materials, such as polymers, fillers, plasticizers, etc., that might otherwise be used in the reagent layer for stability and toughness in the absence of the support film. The support film coated with the reagent layer can be advantageously used to provide biological reagents in a dimensionally stable form, which is sufficiently tough to allow handling, including manufacturing, packaging, transporting, storing, and/or placing in a device in which the reagents are used. Moreover, the support film coated with the reagent layer may be prepared separately from and independently of any device or portion of a device in which the reagent layer may be used.

In one embodiment, there is provided a method of providing at least one reagent for processing sample material, the method comprising:
providing a support film coated with a reagent layer which includes the at least one reagent; and
dimensioning the reagent layer or the reagent layer and support film to fit within at least one chamber of a device for processing sample material; wherein the at least one chamber can contain or channel a fluid.

In another embodiment, there is provided a method of delivering at least one reagent to a device for processing sample material, the method comprising:
providing a support film coated with a reagent layer which includes the at least one reagent;
placing a support film coated with the reagent layer or the reagent layer portion of the support film coated with the reagent layer within at least one chamber of a device for processing sample material, wherein the at least one chamber can contain or channel a fluid, and wherein the reagent layer or the reagent layer and support film are dimensioned to fit within the at least one chamber of the device for processing sample material.

In another embodiment, there is provided a method of adding at least one reagent to at least one step in a process for detecting or assaying a nucleic acid, the method comprising:
providing a support film coated with a dry reagent layer which includes the at least one reagent;
placing the support film coated with the dry reagent layer or the dry reagent layer portion of the support film coated with the dry reagent layer in at least one chamber which can contain or channel a fluid, wherein the at least one step is conducted in the at least one chamber and wherein the at least one step is selected from the group consisting of sample preparation, nucleic acid amplification, and detection; and
contacting the dry reagent layer with a fluid which dissolves, disperses, or suspends the at least one reagent in the reagent layer.

In another embodiment, there is provided a support film coated with a dry reagent layer, wherein the reagent layer or the reagent layer and support film are dimensioned to fit within the at least one chamber of a microfluidic device.

In another embodiment, there is provided a support film coated with a dry reagent layer, wherein the dry reagent layer comprises at least one reagent which can be used in at least one of a step of sample preparation, a step of nucleic acid amplification, and a step of detection in a process for detecting or assaying a nucleic acid.

In another embodiment, there is provided a device for processing sample material, the device having a plurality of chambers which can contain or channel a fluid, wherein a support film coated with a dry reagent layer or the dry reagent layer portion of the support film coated with the dry reagent layer is dimensioned to fit within and is contained within at least one chamber of the device.

The term "comprising" and variations thereof (e.g., comprises, includes, etc.) do not have a limiting meaning where these terms appear in the description and claims.

As used herein, "a," "an," "the," "at least one," and "one or more" are used interchangeably, unless the context clearly dictates otherwise.

Also herein, the recitations of numerical ranges by endpoints include all numbers subsumed within that range (e.g., 5µ to 20µ includes 5, 5.5, 6.0, 6.75, 7.38, 8.72, 10, etc.).

The above summary of the present invention is not intended to describe each disclosed embodiment or every implementation of the present invention. The description that follows more particularly exemplifies illustrative embodiments.

BRIEF DESCRIPTIONS OF THE FIGURES

DETAILED DESCRIPTION OF ILLUSTRATIVE EMBODIMENTS OF THE INVENTION

Figure 1:
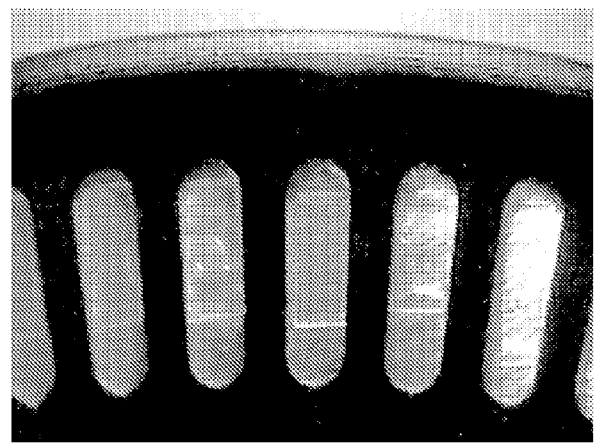
FIG. 1 is a top view of several outer amplification chambers of a microfluidic disc with a dimensioned support film coated with a reagent layer in each chamber.

Biological reagents can now be provided in a reagent layer on a support film which provides dimensional stability and toughness needed during handling, for example, during manufacturing, packaging, storage, and/or placement in a device wherein the biological reagents are used. Toughness relates to resistance to breaking or chipping, such that the reagent layer and support film remain intact.

In one embodiment, there is provided a method of providing at least one reagent for processing sample material, the method comprising:
providing a support film coated with a reagent layer which includes the at least one reagent; and
dimensioning the reagent layer or the reagent layer and support film to fit within at least one chamber of a device for processing sample material; wherein the at least one chamber can contain or channel a fluid.

In another embodiment, there is provided a method of delivering at least one reagent to a device for processing sample material, the method comprising:
providing a support film coated with a reagent layer which includes the at least one reagent;
placing a support film coated with the reagent layer or the reagent layer portion of the support film coated with the reagent layer within at least one chamber of a device for processing sample material, wherein the at least one chamber can contain or channel a fluid, and wherein the reagent layer or the reagent layer and support film are dimensioned to fit within the at least one chamber of the device for processing sample material. For certain embodiments, this method further comprises dimensioning the reagent layer or the reagent layer and support film to fit within the at least one chamber of the device for processing sample material.

In another embodiment, there is provided a method of adding at least one reagent to at least one step in a process for detecting or assaying a nucleic acid, the method comprising:
providing a support film coated with a dry reagent layer which includes the at least one reagent;
placing the support film coated with the dry reagent layer or the dry reagent layer portion of the support film coated with the dry reagent layer in at least one chamber which can contain or channel a fluid, wherein the at least one step is conducted in the at least one chamber and wherein the at least one step is selected from the group consisting of sample preparation, nucleic acid amplification, and detection; and
contacting the dry reagent layer with a fluid which dissolves, disperses, or suspends the at least one reagent in the reagent layer.

In another embodiment, there is provided a support film coated with a dry reagent layer, wherein the reagent layer or the reagent layer and support film are dimensioned to fit within the at least one chamber of a microfluidic device.

In another embodiment, there is provided a support film coated with a dry reagent layer, wherein the dry reagent layer comprises at least one reagent which can be used in at least one of a step of sample preparation, a step of nucleic acid amplification, and a step of detection in a process for detecting or assaying a nucleic acid. For certain embodiments, the dry reagent layer or the dry reagent layer and support film are dimensioned to fit within a chamber which can contain or channel a fluid within a microfluidic device.

For certain embodiments, including any one of the above embodiments where the dry reagent layer or the dry reagent layer and support film are dimensioned to fit within a chamber, the dry reagent layer or the dry reagent layer and support film comprises an area of at least about $0.1\ mm^2$, $1\ mm^2$, $2\ mm^2$, $5\ mm^2$ or $10\ mm^2$. For certain of these embodiments, dry reagent layer or the dry reagent layer and support film comprises an area of at least about $1\ mm^2$, $2\ mm^2$, or $5\ mm^2$. For certain of these embodiments, the dry reagent layer or the dry reagent layer and support film comprises an area of not more than about $1000\ mm^2$, $250\ mm^2$, $100\ mm^2$, $50\ mm^2$, $20\ mm^2$, $15\ mm^2$, or $10\ mm^2$. The shape of the dry reagent layer or the dry reagent layer and support film can be any shape that can be cut from a film or alternatively spot coated on the support film as described below, including a triangle, a square, a rectangle, a trapezoid, a circle, an oval, and a combination thereof.

For certain embodiments, including any one of the above embodiments of the support film coated with the reagent layer or of providing the support film coated with the reagent layer, the dimensioned support film coated with the reagent layer (the reagent layer or the reagent layer and support film are dimensioned) is adhered to a sheet. For certain of these embodiments, a plurality of the dimensioned support films coated with the reagent layer are adhered to the sheet. For certain of these embodiments, the reagent layer is a dry reagent layer. The sheet can be the same or different from the support film. The sheet can be a polymeric film, a metallic sheet, a combination thereof, or the like. The sheet may be comprised of a single layer or multiple layers. The sheet can include an adhesive layer. The sheet can be any suitable shape, for example, a circular disc, a ring, a rectangle, a square, or the like.

In another embodiment, there is provided a device for processing sample material, the device having a plurality of chambers which can contain or channel a fluid, wherein a support film coated with a dry reagent layer or the dry reagent layer portion of the support film coated with the dry reagent layer is dimensioned to fit within and is contained within at least one chamber of the device.

The "sample material" as used herein can be a raw sample material or a processed sample material. Raw sample materials include, for example, clinical samples or specimens (blood, tissue, etc.), food samples (foods, feeds, raw materials for foods or feeds, etc.), environmental samples (water, soil, etc.), or the like. Processed sample materials include, for example, samples containing cells or viruses separated from a raw sample material, and samples containing polynucleotides isolated from cells, viruses, or derived from other sources.

The reagent layer can include at least one reagent which can be used in at least one step of a polynucleotide or nucleic acid manipulation technique or protein processing, including sample preparation and detection steps. For certain embodiments, including any one of the above embodiments, the reagent layer includes at least one reagent which can be used in at least one of a step of sample preparation, a step of nucleic acid amplification, and a step of detection in a process for detecting or assaying a nucleic acid. Sample preparation may include, for example, capturing a biological material containing a nucleic acid, washing a biological material containing a nucleic acid, lysing a biological material containing a nucleic acid, for example, cells or viruses, digesting cellular debris, isolating, capturing, or separating at least one polynucleotide or nucleic acid from a biological sample, and/or eluting a nucleic acid. Nucleic acid amplification may include, for example, producing a complementary polynucleotide of a polynucleotide or a portion of a nucleic acid in sufficient numbers for detection. Detection includes, for example, making an observation, such as detecting a fluorescence, which indicates the presence and/or amount of a polynucleotide or nucleic acid. For certain of these embodiments, the reagent layer includes at least one reagent selected from the group consisting of a lysis reagent, a protein-digesting reagent, a nucleic acid amplifying enzyme, an oligonucleotide, a probe, nucleotide triphosphates, a buffer, a salt, a surfactant, a dye, a nucleic acid control, a reducing agent, dimethyl sulfoxide (DMSO), glycerol, ethylenediaminetetraacetic acid (EDTA), ethylene glycol-bis(2-aminoethylether)-N,N,N',N'-tetraacetic acid (EGTA), microspheres capable of binding a nucleic acid, and a combination thereof. For certain of these embodiments, the group of reagents from which the at least one reagent is selected further includes any one of, any combination of, or all of RNase, DNase, an RNase inhibitor, a DNase inhibitor, Bovine Serum Albumin, spermidine, and a preservative. For certain of these embodiments, the reagent layer includes at least one reagent selected from the group consisting of a nucleic acid amplifying enzyme, an oligonucleotide, a probe, nucleotide triphosphates, a buffer, a salt, and microspheres capable of binding a nucleic acid.

Lysis can be accomplished ezymatically, chemically, and/or mechanically. Enzymes used for lysis include, for example, lysostaphin, lysozyme, mutanolysin, or others. Chemical lysis can be carried out using a surfactant, alkali, heat, or other means. When alkali is used for lysis, a neutralization reagent may be used to neutralize the solution or mixture after lysis. Mechanical lysis can be accomplished by mixing or shearing using solid particles or microparticles such as beads or microbeads. The lysis reagent can include a surfactant or detergent such as sodium dodecylsulfate, lithium dodecylsulfate, or N-methyl-N-(1-oxododecyl)glycine, sodium salt, or the like, buffered as needed; a chaotrope such as guanidium hydrochloride, guanidium thiacyanate, sodium iodide, or the like; a lysis enzyme such as lysozyme, lysostaphin, mutanolysin, proteinases, pronases, cellulases, or any of the other commercially available lysis enzymes; an alkaline lysis reagent; a neutralization reagent, solid particles such as beads, or a combination thereof.

The protein-digesting reagent can facilitate digestion of proteins present in the sample material, including a lysis enzyme if present. In addition, the protein-digesting reagent, for example, proteinase K, can act as a lysis reagent in the presence of a surfactant.

"Nucleic acid amplifying enzyme" refers to an enzyme which can catalyze the production of a polynucleotide or a nucleic acid from an existing DNA or RNA template. For certain embodiments, the nucleic acid amplifying enzyme is an enzyme that can be used in a process for amplifying a nucleic acid or a portion of a nucleic acid. For certain embodiments, the nucleic acid amplifying enzyme is selected from the group consisting of a DNA polymerase and a reverse transcriptase. For certain embodiments, the DNA polymerase is selected from the group consisting of Taq DNA polymerase, Tfl DNA polymerase, Tth DNA polymerase, Tli DNA polymerase, and Pfu DNA polymerase. For certain of these embodiments, the reverse transcriptase is selected from the group consisting of AMV reverse transcriptase, M-MLV reverse transcriptase, and M-MLV reverse transcriptase, RNase H minus Retroviral reverse transcriptase, such as M-MLV and AMV posses an RNA-directed DNA polymerase activity, a DNA directed polymerase activity, as well as an RNase H activity. For certain embodiments, the nucleic acid amplifying enzyme is a DNA polymerase or an RNA polymerase. For certain embodiments, the nucleic acid amplifying enzyme is Taq DNA polymerase. For certain embodiments, the nucleic acid amplifying enzyme is T7 RNA polymerase.

The "oligonucleotide" can be a primer, a terminating oligonucleotide, an extender oligonucleotide, or a promoter oligonucleotide. For certain embodiments, the oligonucleotide is a primer. Such oligonucleotides typically comprised of 15 to 30 nucleotide units, which determines the region (targeted sequence) of a nucleic acid to be amplified. Under appropriate conditions, the bases in the primer bind to complementary bases in the region of interest, and then the nucleic acid amplifying enzyme extends the primer as determined by the targeted sequence. A large number of primers are known and commercially available, and others can be designed and made using known methods.

Probes allow detection of amplification products (amplicons) by fluorescing, and thereby generating a detectable signal, the intensity of which is dependent upon the number of fluorescing probe molecules. Probe molecules can be comprised of an oligonucleotide and a fluorescing group coupled with a quenching group. Probes can fluoresce when separation or decoupling of the quenching group and the fluorescing group occurs upon binding to an amplicon or upon nucleic acid amplifying enzyme cleavage of the probe bound to the amplicon. Alternatively, a probe bound to the amplicon can fluoresce upon exposure to light of an appropriate wavelength. For certain embodiments, including any one of the above embodiments, the probe is selected from the group consisting of TAQMAN probes (Applied Biosystems, Foster City, Calif.), molecular beacons, SCORPIONS probes (Eurogentec Ltd., Hampshire, UK), SYBR GREEN (Invitrogen, Carlsbad, Calif.), FRET hybridization probes (Roche Applied Sciences, Indianapolis, Ind.), Quantitect probes (Qiagen, Valencia, Calif.), and molecular torches.

The nucleotide triphosphates (NTPs), including ribonucleotide triphosphates and deoxyribonucleotides triphosphates as required, are used by the nucleic acid amplifying enzyme in the production of a polynucleotide or a nucleic acid from an existing DNA or RNA template. For example, when amplifying a DNA, a dNTP (deoxyribonucleotide triphosphate) set is used, which typically includes dATP (2'-deoxyadenosine 5'-triphosphate), dCTP (2'-deoxycytodine 5'-triphosphate), dGTP (2'-deoxyguanosine 5'-triphosphate), and dTTP (2'-deoxythimidine 5'-triphosphate).

Buffers are used to regulate the pH of the reaction media. A wide variety of buffers are known and commercially available. For example, morpholine buffers, such as 2-(N-morpholino)ethanesulfonic acid (MES), can be suitable for providing an effective pH range of about 5.0 to 6.5, imidazole buffers can be suitable for providing an effective pH range of about 6.2 to 7.8, and tris(hydroxymethyl)aminomethane (TRIS) buffers and certain piperazine buffers such as N-(2-hydroxyethyl)piperazine-N'-(2-ethanesulfonic acid) (HEPES) can be suitable for providing an effective pH range of about 7.0 to 9.0. The buffer can affect the activity and fidelity of nucleic acid amplifying enzymes, such as polymerases. For certain embodiments, the buffer is selected from at least one buffer which can regulate the pH in the range of 7.5 to 8.5. For certain of these embodiments, the buffer is a TRIS-based buffer. For certain of these embodiments, the buffer is selected from the group consisting of at least one of TRIS-EDTA, TRIS buffered saline, TRIS acetate-EDTA, and TRIS borate-EDTA. Other materials can be included with these buffers, such as surfactants and detergents, for example, CHAPS or a surfactant described below. For certain embodiments, the buffers are free of RNase and DNase.

Salts can affect the activity of nucleic acid amplifying enzymes. For example, free magnesium ions are necessary for certain polymerases, such as Taq DNA polymerase, to be active. In another example, in the presence of manganese ions, Tfl DNA polymerase and Tth DNA polymerase can catalyze the polymerization of nucleotides into DNA, using RNA as a template. In a further example, the presence of certain salts, such as potassium chloride, can increase the activity of certain polymerases such as Taq DNA polymerase. For certain embodiments, including any one of the above embodiments, the salt is selected from the group consisting of at least one of magnesium, manganese, zinc, sodium, and potassium salts. For certain of these embodiments, the salt is at least one of magnesium chloride, manganese chloride, zinc sulfate, zinc acetate, sodium chloride, and potassium chloride. For certain of these embodiments, the salt is magnesium chloride.

A surfactant can be included for lysing or de-clumping cells, improving mixing, enhancing fluid flow, for example, in a device, such as a microfluidic device. The surfactant can be non-ionic, such as a poly(ethylene oxide)-poly(propylene oxide) copolymer available, for example, under the trade name PLURONIC, polyethylene glycol (PEG), polyoxyethylenesorbitan monolaurate available under the trade name TWEEN 20, 4-(1,1,3,3-tetramethylbutyl)phenyl-polyethylene glycol available under the trade name Triton X-100; anionic, such as lithium lauryl sulfate, N-lauroylsarcosine sodium salt, and sodium dodecyl sulfate; cationic, such as alkyl pyridinium and quaternary ammonium salts; zwitterionic, such as N—($C_{10}$-$C_{16}$ alkyl)-N,N-dimethylglycine betaine (in the betaine family of surfactants); and/or a fluoro surfactant such as FLUORAD-FS 300 (3M, St. Paul, Minn.) and ZONYL (Dupont de Nemours Co., Wilmington, Del.).

A dye can be included in the reagent layer to impart a color or a fluorescence to the reagent layer or to a fluid which contacts the reagent layer. The color or fluorescence can provide visual evidence or a detectable light absorption or light emission evidencing that the reagent layer has been dissolved, dispersed, or suspended in the fluid which contacts the reagent layer. For certain embodiments, the dye is selected from the group consisting of fluorescent dyes, such as fluorescein, cyanine (which includes Cy3 and Cy5), Texas Red, ROX, FAM, JOE, SYBR Green, OliGreen, and HEX. In addition to these fluorescent dyes, ultraviolet/visible dyes, such as dichlorophenol, indophenol, saffranin, crystal violet, and commercially-available food coloring can also be used.

A nucleic acid control is a known amount of a nucleic acid or nucleic acid containing material dried-down with either the sample preparation or the amplification or detection reagents. This internal control can be used to monitor reagent integrity as well as inhibition from the sample material or specimen. Linearized plasmid DNA control is typically used as a nucleic acid internal control.

The reducing agent is a material capable of reducing disulfide bonds, for example in proteins which can be present in a sample material or specimen, and thereby reduce the viscosity and improve the flow and mixing characteristics of the sample material. For certain embodiments, the reducing agent preferably contains at least one thiol group. Examples of reducing agent include N-acetyl-L-cysteine, dithiothreitol, 2-mercaptoethanol, and 2-mercaptoethylamine.

Dimethyl sulfoxide (DMSO) can be used to inhibit the formation of secondary structures in the DNA template; glycerol can improve the amplification process, can be used as a preservative, and can stabilize enzymes such as polymerases; ethylenediaminetetraacectic acid (EDTA) and ethylene glycol-bis(2-aminoethylether)-N,N,N'N'-tetraacetic acid (EGTA) can be used as metal ion chelators and also to inactivate metal-binding enzymes (RNAses) that may damage the reaction.

RNase or DNase may be used to break down undesired RNA or DNA which is present in a sample material. For example, when DNA is being targeted, RNA which may be present can be rendered non-interfering with RNase; and likewise, when RNA is being targeted, DNA which may be present can be rendered non-interfering with DNase. Alternatively, when RNase and/or DNase may be present, but are undesired because of their ability to break down a targeted RNA or DNA, an RNase inhibitor or a DNase inhibitor or both may be used to prevent such break down. a preservative Bovine Serum Albumin can be used to stabilize the nucleic acid amplifying enzyme during nucleic acid amplification.

For amplification, certain compounds may be added to stimulate the amplifying enzyme. For example, spermidine may be used to stimulate RNA polymerase.

Although the reagent layer is dried down as described below, the reagent layer may include a preservative to inhibit or prevent inadvertent microbial growth in the reagent layer. For example, a synthetic preservative such as methyl paraben, propyl paraben, sodium azide, or the like may be used for this purpose.

The term "microspheres" refers to microspheres, microparticles, microbeads, resin particles, and the like. Microspheres capable of binding a nucleic acid can be useful in a sample preparation step where, for example, at least one polynucleotide or nucleic acid is isolated or separated from a biological sample. Examples of microspheres capable of binding a polynucleotide or nucleic acid include resin and silica particles with metal ions immobilized on the surface of the resin or silica particles. Resin particles can be latex beads, polystyrene beads, and the like. The resin or silica particles can be magnetic or non-magnetic. The particles can be colloidal in size, for example about 100 nm, to about 10μ. Such immobilized metal resin particles can be made as described in U.S. Pat. No. 7,112,552 at Examples 1 and 2; U.S. Patent Publication No. 2004/0152076 at paragraph 0152, and in U.S. Ser. No. 60/913,812, titled COMPOSITIONS, METHODS, AND DEVICES FOR ISOLATING BIOLOGICAL MATERIALS, filed Apr. 25, 2007. Microspheres can also be used for resuspension and mixing of sample preparation, amplification, or detection reagents. For example, glass or magnetic beads without or with binding capability can be used for this purpose.

For certain embodiments, including any one of the above embodiments, the reagent layer includes at least one reagent selected from the group consisting of a nucleic acid amplifying enzyme, a primer, a probe, and microspheres capable of binding a nucleic acid. For certain embodiments, including any one of the above embodiments, the reagent layer includes at least one reagent selected from the group consisting of a nucleic acid amplifying enzyme, a primer, and a probe. For certain of these embodiments, the reagent layer includes a nucleic acid amplifying enzyme. In these embodiments, nucleic acid amplifying enzyme, primer, and probes can include any one of the embodiments described above for each of these reagents.

For certain embodiments, including any one of the above embodiments, the reagent layer further includes a matrix material selected from the group consisting of a water soluble polymer, a carbohydrate and a combination thereof. As used herein, "water soluble" means that material, for example, the water soluble polymer, carbohydrate, or a combination thereof, can be dissolved, dispersed, or suspended in water at a temperature that is at least room temperature. For certain embodiments, the temperature is at least 50° C. For certain embodiments, the temperature is not more than 100° C., preferably not more than 97° C., more preferably not more than 75° C. The matrix material can hold or contain at least one reagent. The matrix material can also increase adhesion of the reagent layer to the support film and allow the reagent layer to be coated in a wider range of thicknesses than would otherwise be possible. The ability to prepare the reagent layer in a wide range of thicknesses allows a wider range of reagent amounts to be provided. For certain of these embodiments, the matrix material is a water soluble polymer. For certain of these embodiments, the water soluble polymer is selected from the group consisting of poly(ethylene glycol), poly(vinyl alcohol), partially hydrolyzed poly(vinyl alcohol), polyvinylpyrrolidone, poly(1-vinylpyrrolidone-co-2-dimethylaminoethylmethacrylate), poly(1-vinylpyrrolidone-co-vinyl acetate), and a combination thereof. For certain of these embodiments, the water soluble polymer is selected from the group consisting of poly(vinyl alcohol), poly(vinyl alcohol acetate), polyvinylpyrrolidone, and a combination thereof. For certain of these embodiments, the water soluble polymer is polyvinyl alcohol) which is at least 80% hydrolyzed. For certain of these embodiments, the polyvinyl alcohol) is at least 90% hydrolyzed and has a weight average molecular weight of about 30,000 to about 70,000.

For certain embodiments, the matrix material is a carbohydrate. For certain of these embodiments, the carbohydrate is selected from the group consisting of sucrose, trehalose, mannitol, sorbitol, raffinose, stachyose, melezitose, dextrose, maltose, dextran, cellobiose, pectin, hydroxyethylcellulose, hydroxypropylcellulose, hydroxypropylmethylcellulose, guar gum, locust gum, gum arabic, xanthan gum, ficoll, a poly(ethylene oxide)-poly(propylene oxide) copolymer with a hydrophilic/lipophilic balance of greater than 7, preferably greater than 9, more preferably about 12, a cyclodextrin, α-cyclodextrin, starch, pullulan, alginates, gelatins, and carrageenans. For certain of these embodiments, the carbohydrate is selected from the group consisting of sucrose, dextran, trehalose, pullulan, α-cyclodextrin, mannitol, sorbitol, and a combination thereof. For certain embodiments, the carbohydrate is a sugar.

For certain of these embodiments, the matrix material is a combination of a water soluble polymer and a carbohydrate. In these embodiments, the water soluble polymer and the carbohydrate can be independently selected from any one of the above embodiments.

The reagent layer can further include additional optional components, such as fillers and plasticizers. If included, additional optional components are used in minimal amounts and, preferably do not interfere with the activity or function of any of the reagents.

For certain embodiments, including any one of the above embodiments, the reagent layer is comprised of more than one layer. Each layer can contain the same or different reagents or the same or different matrix components (i.e., water soluble polymers, carbohydrates, or other optional components). Alternatively, where the reagent layer is comprised of more than one layer, one or more layers can contain no reagent, for example, a top layer and/or a layer disposed between two layers containing reagents, and/or a layer disposed between a layer containing at least one reagent and the support film.

For certain embodiments, the support film does not fluoresce at wavelengths of light used for detection. For certain embodiments, preferably the support film does not fluoresce to an appreciable extent and is transparent to or does not appreciably absorb the light used to bring about fluorescence in a probe or the light emitted during fluorescence of a probe.

The support film is preferably chosen such that a major surface of the support film adheres to the reagent layer such that the reagent layer does not easily release from or is not easily separated from the support film during manufacturing, packaging, storage, and/or placement in a device. The reagent layer remains adhered to the support film until the reagent in the reagent layer is dissolved, dispersed, or suspended when finally used. For certain embodiments, the support film includes an adhesion promoting layer on a major surface of the support film, such that the adhesion promoting layer contacts the reagent layer. For certain of these embodiments, the adhesion promoting layer is a pressure sensitive adhesive layer. The adhesion promoting layer is selected to have the same light transmission and non-fluorescing properties as described above for the support film.

The support film is sufficiently rigid to be dimensionally stable during coating, dimensioning (for example, die cutting), and placement in a device. By "dimensionally stable" is meant that the support film maintains its shape and dimensions within about 5%, preferably within about 1%, of the support films dimensions prior to coating.

For certain embodiments, including any one of the above embodiments, preferably the support film is substantially insoluble in water. Substantially insoluble means that less than 10%, 5%, 1%, 0.1%, or 0.01% by weight of the support film is lost. The support film is substantially insoluble in water at a temperature up to room temperature, at a temperature up to 60° C., or at a temperature up to 100° C. Preferably, less than 0.01% by weight is lost at a temperature up to 97° C. This property avoids excessive amounts of superfluous or interfering materials from entering into the reaction mixture in which the reagent must function. The support film is inert with respect to the reagent in the reagent layer, and does not appreciably interfere with the function of the reagent.

For certain embodiments, including any one of the above embodiments, the support film is a low-fluorescing film comprised of a polymer selected from the group consisting of a polyester, a polycarbonate, a polypropylene, a polyethylene, a poly(vinyl acetate), a poly(acrylate), a poly(methacrylate), and a combination thereof. For certain of these embodiments the support film is comprised of oriented polypropylene, polyester, or polyolefin.

In an alternative embodiment, the support film can be a metallic sheet coated with adhesive. The metallic sheet can be non-magnetic, such as an aluminum or copper sheet. The adhesive can prevent the metal or metals in the sheet from interfering with or contaminating the reagent layer. The adhesive can also increase the adhesion of the reagent layer to the metallic sheet. The adhesive can be a low-fluorescing adhesive to minimize interference with detection.

The low-fluorescing film and low-fluorescing adhesive mentioned above do not fluoresce appreciably or do not fluoresce at wavelengths of light used for detection.

The support film can be coated with a solution, slurry, suspension, or the like, which contains the at least one reagent, using a variety of known coating methods, followed by removal of a portion, for example, at least 50%, 75%, 90%, 99%, or all of the solvent or fluid used for the slurry, suspension, or the like to form the reagent layer. The reagent layer that is coated on the support film may be deposited with minimal use of additives that would otherwise be needed to produce a mechanically and chemically stable layer. Since such additives can potentially interfere with either the sample preparation, amplification, or detection methods, using reduced levels of these additives can be advantageous for carrying out these methods.

Drying methods such as freeze drying, vacuum drying, and air (or inert gas) drying at room temperature or an elevated temperature, such as forced air drying, can be used to remove the solvent or fluid after coating. The solvent or fluid is preferably water. Known coating methods include die coating, roll coating, reverse roll coating, wire-wound rod coating, spraying, spot coating, and the like.

Spot coating includes dispensing a spot of a size that includes sufficient reagent for carrying out a desired reaction in one chamber. An inkjet, pipette, or similar means can be used for dispensing the spot in any of a wide variety of amounts, shapes, or configurations. The spot can be dispensed as a liquid or a solid, such as a powder or a granular solid. The powder or granular solid can be compacted on the support film, for example, by roller compaction.

The shape and/or configuration of the reagent layer produced by spot coating can be influenced by first treating the surface of the support film. Treatments such as plasma, chemical vapor deposition, embossing, or coating can be used to modify the wetting characteristics of the support film or otherwise control the total area and shape of the area covered by the spot during coating and drying.

For certain embodiments, including any one of the above embodiments, the support film coated with the reagent layer has a thickness of not more than about 250µ, 200µ, 150µ, 100µ, or 50µ, and wherein the thickness includes both the support film and the reagent layer. For certain of these embodiments, the thickness is at least about 10µ, 20µ, 25µ, or 50µ. For certain of these embodiments, the reagent layer has a thickness of not more than about 50µ, 25µ, 20µ, 15µ, 10µ, 5µ, or 1µ. For certain of these embodiments, the reagent layer has a thickness of up to about 50µ, for example, when the reagent layer includes microspheres or beads.

Dimensioning the support film coated with the reagent layer (by either dimensioning the reagent layer or the reagent layer and support film) to fit within at least one chamber of the device for processing sample material can be accomplished by a variety of methods. For example, a rule die, rotary die cutter, or a punch can be made and used for cutting the coated support film into pieces sized to fit within the at least one chamber. In another example, a sheet of coated support film can be cut or slit into strips in one direction. Individual pieces, sized as above, can then be cut from each strip, thereby dicing the coated support film. In another example, a sheet of coated support film can be scored into strips in one direction and then slit into strips in a cross direction. Individual pieces, sized as above, can then be easily cut or broken off of the resulting strips at the score lines. The piece size can further be determined and established to provide a pre-determined amount of a reagent. For example, with a known amount of reagent in a given area of the reagent layer, the size required for a particular or pre-determined amount of reagent can be determined and used. A pre-determined amount of reagent is an amount of reagent sufficient to carry out a step or provide conditions for carrying out a step associated with sample preparation, nucleic acid amplification, detection, or a combination thereof.

The reagent layer can also be dimensioned using the spot coating described above, thereby providing a pre-determined amount of a reagent in a defined area on the support film. For example, the solution, slurry, suspension, or the like which contains the at least one reagent can be dispensed at discrete locations on the support film. After drying, the resulting spots or areas containing the at least one reagent can be individually cut out by cutting the surrounding support film to fit within a chamber. Alternatively, the spot or area containing the at least one reagent can be dimensioned not only to provide a pre-determined amount of the at least one reagent, but also to fit within an opening into a chamber, such that the reagent layer is within the chamber while the support film may also be within the chamber, or, although not within the chamber, may form an interior surface of the chamber at the opening. For certain embodiments, including any one of the above embodiments, the support film coated with the reagent layer is further dimensioned to provide a pre-determined amount of at least one reagent.

For certain embodiments, including any one of the above embodiments of a method which includes providing and dimensioning the support film coated with the reagent layer, the method further comprises adhering the dimensioned support film coated with the reagent layer to a sheet. In such embodiments, the major surface of the support film, which is not coated with the reagent layer, can be adhered to the sheet. The sheet can be the same as or different from the support film. The sheet can be a polymeric film, a metallic sheet, a combination thereof, or the like. The sheet may be comprised of a single layer or multiple layers. The sheet can include an adhesive layer.

A pressure sensitive adhesive, hot melt adhesive, thermoset adhesive, thermal bonding, static charge, or other like means can be used to adhere the support film to the sheet. The degree to which the support film adheres to the sheet can be controlled, such that the dimensioned support film coated with the reagent layer can be removed from the film or sheet for placement in a reaction chamber, or the dimensioned support film coated with the reagent layer adhered to the film or sheet can be used in combination. In the latter case, the sheet can define a portion of the chamber with the support film coated with the reagent layer positioned within the chamber.

The at least one chamber of the device for processing sample material can be, for example, a micro-centrifuge tube, a cuvette, microcuvette, well, microwell, or the like. The chamber can be equipped without or with an opening, without or with an inlet channel, and/or without or with an outlet channel. The chamber can serve as a depot for adding a reagent to a fluid stream, or the chamber can be a place where an action takes place such as mixing, washing, extracting, a reaction, and/or the like.

As indicated above, the support film coated with the reagent layer is dimensioned to fit within the chamber. That is, the reagent layer or the reagent layer and support film are dimensioned to fit within the chamber. For certain embodiments, an entire major surface of the support film is coated with the reagent layer, and the area of the support film which is coated with the reagent layer and the area of the support film have the same dimensions to fit within the chamber. Alternatively, for certain embodiments, a portion of a major surface of the support film is coated with the reagent layer, and the area of the support film which is coated with the reagent layer is dimensioned to fit within the chamber. For certain of these embodiments, the support film, including the area of the support film which is coated with the reagent layer and an area of the support film which is not coated with the reagent layer, is dimensioned to fit within the chamber. The dimensions of the reagent layer or the reagent layer and support film are less than the corresponding dimensions of the chamber, allowing space between the walls of the chamber and the edges and major surfaces of the dimensioned reagent layer or the reagent layer and support film. This allows easy placement of the dimensioned reagent layer or the reagent layer and support film within the chamber without getting caught or hung-up on the walls of the chamber during placement. This also allows for additional space within the chamber for a fluid, such as an aqueous fluid containing a sample material or a component of a sample material. The fluid can, thereby, be quickly moved into the chamber, completely cover or contact the entire reagent layer, and undergo fluid mixing with the reagent(s) in the reagent layer, dissolving, dispersing, or suspending the reagent(s) in the reagent layer.

The device for processing sample material may provide a location or locations and conditions for any one or all of the steps of a polynucleotide or nucleic acid manipulation technique or protein processing, including sample preparation and detection steps. The device for processing sample material may provide a location or locations and conditions for any one or all of the steps of sample preparation, nucleic acid amplification, and detection. The sample material may be located in one or a plurality of chambers. The device may provide uniform and accurate temperature control of the chamber or chambers. The device may provide channels between chambers, for example, such that sample preparation may take place in one or more chambers, and the nucleic acid amplification and detection may take place in another chamber. For certain embodiments, including any one of the above embodiments, the at least one chamber capable of containing or channeling a fluid is within a microfluidic device. For certain embodiments, including any one of the above embodiments which include the device for processing sample material, the device for processing sample material is a microfluidic device. Some examples of microfluidic devices are described in U.S. Publication Numbers 2002/0064885 (Bedingham et al.); US2002/0048533 (Bedingham et al.); US2002/0047003 (Bedingham et al.); and US2003/138779 (Parthasarathy et al.); as well as U.S. Pat. Nos. 6,627,159; 6,720,187; 6,734,401; 6,814,935; 6,987,253; 7,026,168, and 7,164,107.

Figure 2:
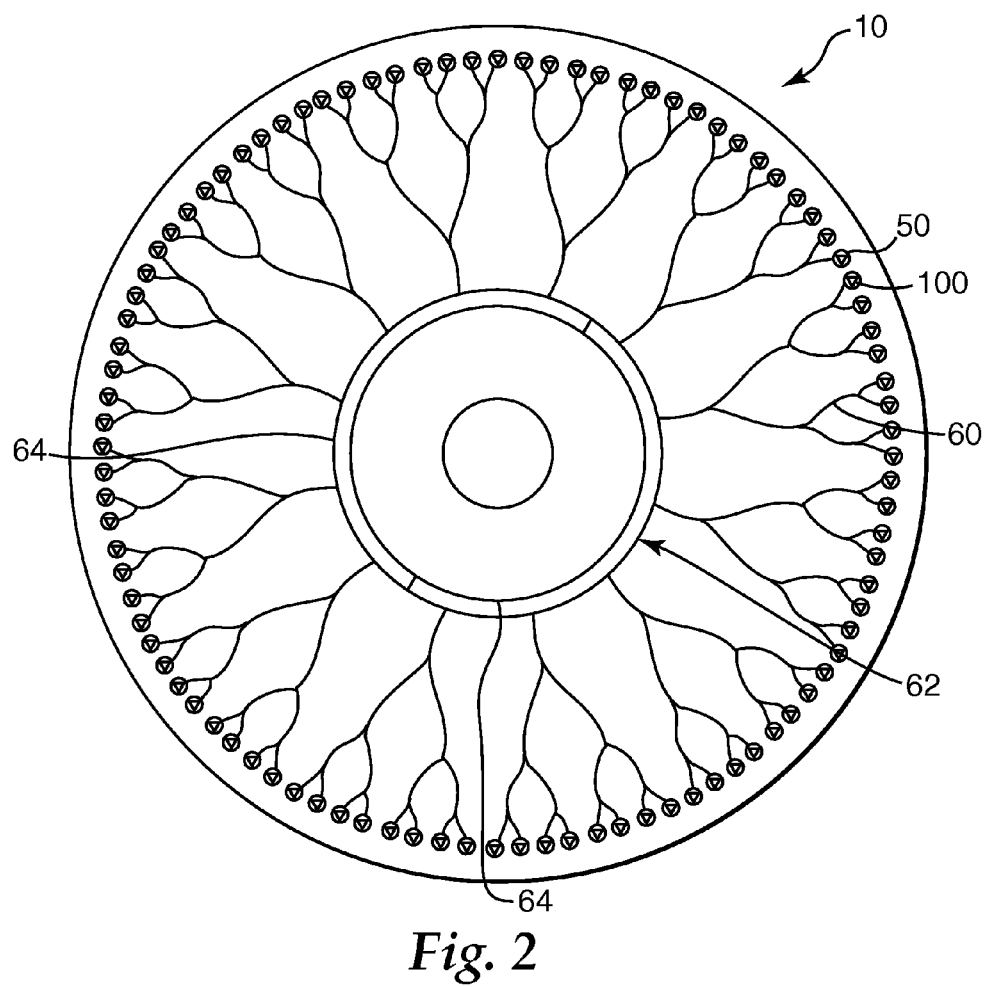
FIG. 2 is a top view of a microfluidic device with a dimensioned support film coated with a reagent layer in each of the outer chambers of the device.
Figure 3:
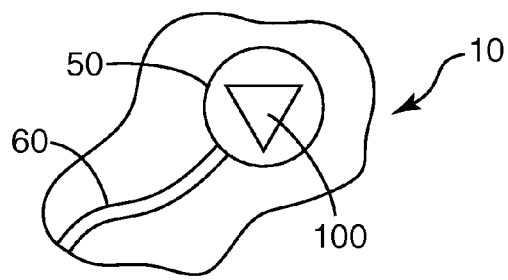
FIG. 3 is a top plan view of a chamber within a microfluidic device with a dimensioned support film coated with a reagent layer placed in the chamber.
Figure 4:
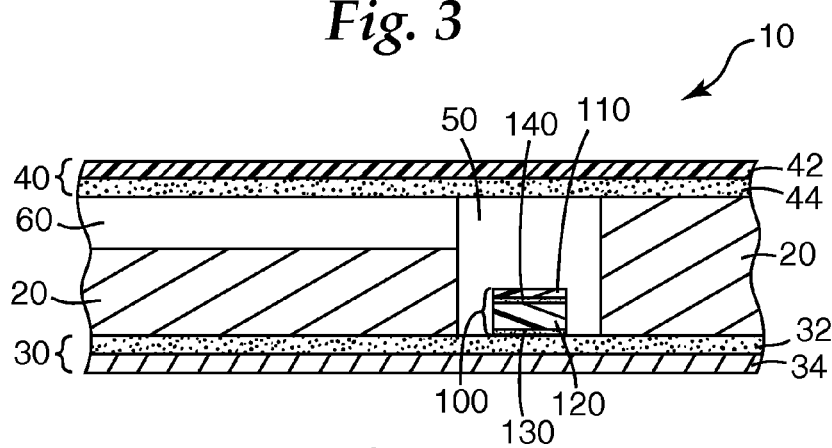
FIG. 4 is a cross-sectional view of a chamber within a microfluidic device with a dimensioned support film coated with a reagent layer placed in the chamber.

One illustrative device for processing sample material is the microfluidic device depicted in FIGS. 2, 3, and 4. The device 10 can be in the shape of a circular disc as illustrated in FIG. 2, although other shapes can be used. Preferred shapes are those that can be rotated. The device 10 of FIGS. 2, 3, and 4 is comprised of multiple layers, including a substrate 20, a first layer 30, and a second layer 40 (as shown in FIG. 4).

The device 10 includes a plurality of chambers 50, each of which defines a volume for containing a fluid. The illustrated device 10 of FIG. 2 includes ninety-six chambers 50, although the number of chambers can be as few as one or more than ninety-six.

The chambers 50 are shown in the form of a chamber that can contain a fluid, although the chambers 50 can be in a form that channels a fluid (e.g., capillaries, passageways, channels, grooves), that is, allows fluid to pass through the chamber.

The substrate 20, the first layer 30, and the second layer 40 are preferably bonded or attached together to contain a fluid (e.g., an aqueous fluid) without leakage of the fluid through the bond or attachment between the substrate 20 and the first layer 30 or the second layer 40. The bond or attachment can be, for example, a pressure sensitive adhesive, hot melt adhesive, thermoset adhesive, or a thermal bond. In FIG. 4, optional layer 32 can bond first layer 30 to substrate 20, and optional adhesive layer 44 can bond second layer 40 to substrate 20.

FIGS. 2, 3, and 4 also illustrate a dimensioned support film coated with a reagent layer 100 located within the process chamber(s) 50. The dimensioned support film coated with a reagent layer 100 is illustrated in the shape of a triangle. However, any convenient shape may be used, such that the dimensioned support film coated with the reagent layer 100 allows sufficient space between the edges of the dimensioned support film coated with the reagent layer 100 and the walls of the chamber for ready placement entirely within the chamber, and a fluid can readily contact the entire surface of the reagent layer 110. Moreover, although FIGS. 2, 3, and 4 show one dimensioned support film coated with a reagent layer 100 within the process chamber(s) 50, more than one dimensioned support film coated with a reagent layer 100 can be within the process chamber(s) 50. Each reagent layer 100 can contain a different reagent or a different combination of reagents.

FIG. 2 illustrates all of the chambers 50 having a dimensioned support film coated with a reagent layer 100 within the chambers 50. However, at least one but less than all of the chambers 50 can have a dimensioned support film coated with a reagent layer 100. Each dimensioned support film coated with a reagent layer 100 can contain the same reagents, some can contain the same reagent or set of reagents while others contain a different reagent or set of reagents, or each can contain a different reagent or set of reagents.

FIG. 4 illustrates the dimensioned support film coated with the reagent layer 100 contacting the first layer 30, although the dimensioned support film coated with the reagent layer 100 can be placed in the chamber 50 so as to be in contact with any one of the walls of the chamber 50, including the second layer 40. The dimensioned support film coated with the reagent layer 100 can be adhered to one of the walls of the chamber 50 by an optional adhesive layer 130 provided on the major surface of the support film 120 opposite the major surface of the support film 120 having the reagent layer 110 thereon. Instead of or in addition to optional adhesive layer 130, optional layer 32 can be an adhesive layer which can adhere the dimensioned support film coated with the reagent layer 100 to the first layer 30. In another alternative, instead of or in addition to adhesive layer 130, optional adhesive layer 44 can adhere the dimensioned support film coated with the reagent layer 100 to the second layer 40. Optional layer 32, optional adhesive layer 44, and optional adhesive layer 130 can be a pressure sensitive adhesive, hot melt adhesive, thermoset adhesive, or a thermal bond. For certain embodiments, any one or all of these layers are preferably a pressure sensitive adhesive.

In the illustrated device 10 of FIGS. 2, 3, and 4, the chambers 50 are in fluid communication with channels 60 which are also in fluid communication with supply chamber 62. Supply chamber 62 can supply a fluid (e.g., a sample material, a buffer, or the like) to channels 60 and chambers 50. The channel 60 is formed in the substrate 20. In FIG. 4, the channel 60 is enclosed by layer 40, although channel 60 can instead be on the opposite side of substrate 20 and be enclosed by layer 30.

In the illustrated device 10 of FIG. 2, the supply chamber 62 is divided into two subchambers 64 that are isolated from each other. This allows a different material, for example a sample material or a buffer, to be introduced into each subchamber 64 for distribution to chambers 50 by way of channels 60. Although two subchambers 64 are shown in FIG. 2, there can be no subchambers 64 or there can be more than two subchambers 64, for example, as many subchambers as channels 60.

In the illustrated device of FIG. 4, a first layer 30 is provided on one side of the substrate 20 and includes a layer 34. The layer 34 can be comprised of one layer or multiple layers, can be a polymeric film such as described herein for the support film, can be a metallic layer, or a combination of a polymeric film and a metallic layer. When the layer 34 is a metallic layer, optional layer 32 may be present to separate the chamber 50 from the metal of the metallic layer.

In the illustrated device of FIG. 4, a second layer 40 is provided on one side of the substrate 20 and includes a layer 42. The layer 42 can be comprised of one layer or multiple layers, can be a polymeric film such as described herein for the support film, can be a metallic layer, or a combination of a polymeric film and a metallic layer. When the layer 42 is a metallic layer, optional layer 44 may be present to separate the chamber 50 from the metal of the metallic layer, and layer 34 is preferably other than a metallic layer, thereby providing the capability of detecting fluorescence through layer 34. Layer 42 is preferably other than a metallic layer, and may provide the capability of detecting fluorescence through layer 42.

Figure 5:
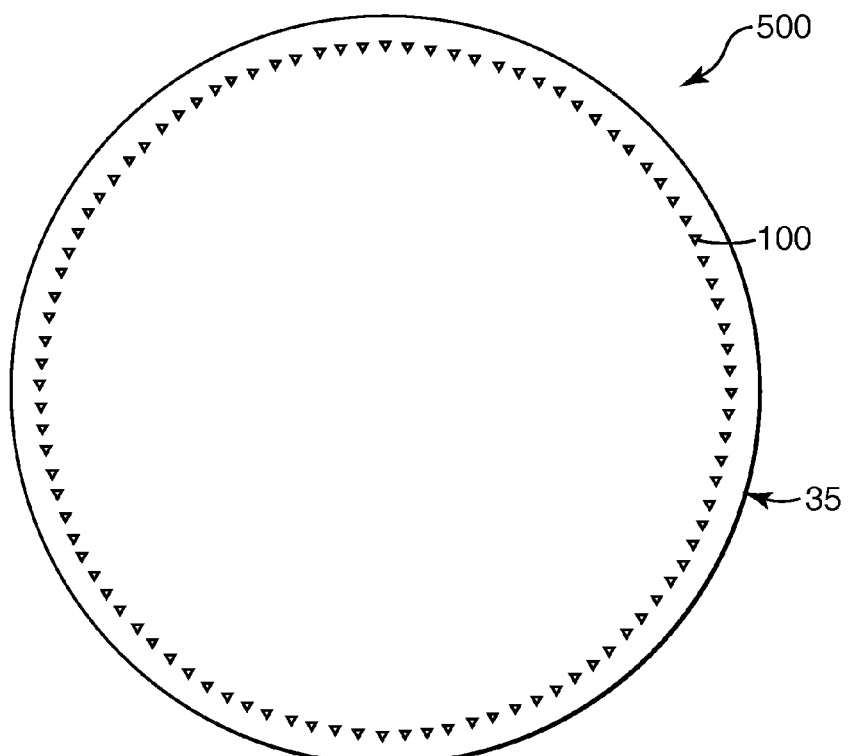
FIG. 5 is a top view of a plurality of dimensioned support films coated with a reagent layer adhered to a plurality of positions on a sheet.
Figure 6:
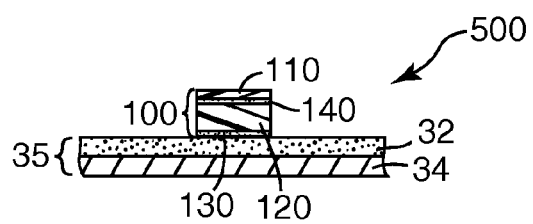
FIG. 6 is a cross-sectional view of a dimensioned support film coated with a reagent layer adhered to a sheet.

FIGS. 5 and 6 illustrate a supported reagent layer array 500 having a plurality of dimensioned support films coated with the reagent layer 100 adhered to a sheet 35. The sheet 35 may be used for the first layer 30 or the second layer 40 shown in FIG. 4. The sheet 35 can be the shape of a circular disc as illustrated in FIG. 5, although other shapes can be used. Preferred shapes are those that can be used for first layer 30 or second layer 40 in a device such as device 10, one embodiment of which is illustrated in FIG. 2. Each of the dimensioned support films coated with the reagent layer 100 adhered to sheet 35 are positioned to fit within a chamber 50 when sheet 35 is used for the first layer 30 or the second layer 40 of device 10 as shown, for example, in FIG. 4. The sheet 35 can be as described for layer 30 above.

A single dimensioned support film coated with the reagent layer 100 in the array 500 is illustrated in FIG. 6. The sheet 35, layer 34, optional layer 32, optional adhesive layer 130, support film 120, reagent layer 110, and dimensioned support film coated with the reagent layer 100 are as described above.

In the illustrated devices shown in FIGS. 4 and 6, an optional adhesion promoting layer 140 can be included between reagent layer 110 and support film 120.

Figure 7:
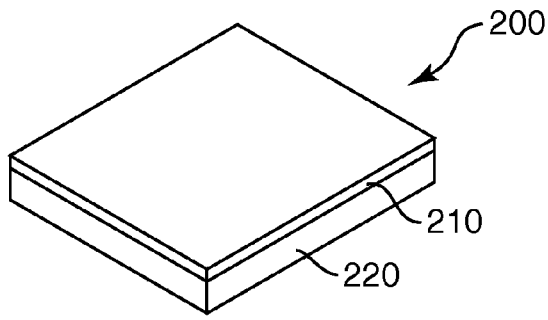
FIG. 7 is a perspective view of a support film coated with a reagent layer.

In FIG. 7, a support film coated with a reagent layer 200 is illustrated in the shape of a square or rectangle, although other shapes can be used. The reagent layer 210 covers one major surface of support film 220. The support film coated with the reagent layer 200 can be dimensioned to fit within a chamber 50 shown in FIGS. 2, 3, and 4 or it can comprise an area large enough to fabricate a number of dimensioned support films coated with the reagent layer, such as the dimensioned support film coated with the reagent layer 100 shown in FIGS. 2, 3, and 4.

Figure 8:
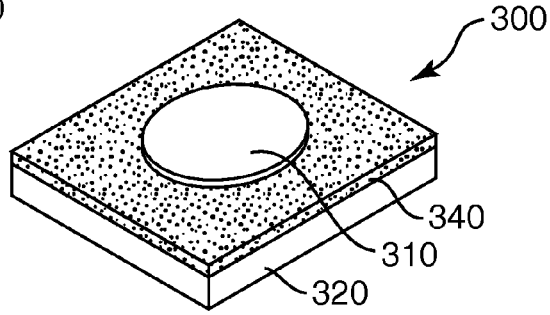
FIG. 8 is a perspective view of an alternative support film coated with a reagent layer, wherein the reagent layer covers a portion of the support film.
Figure 10:
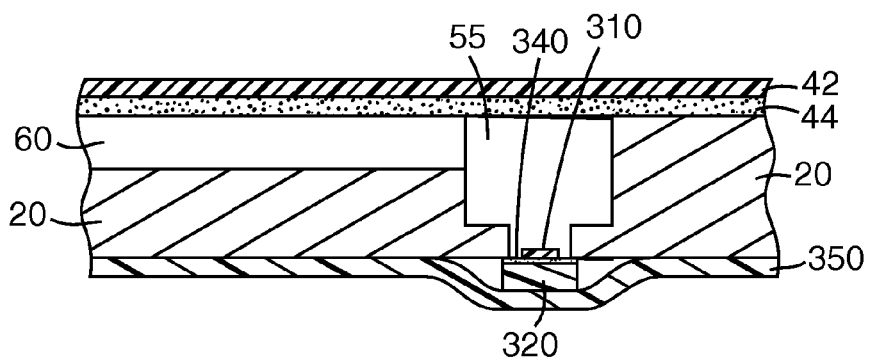
FIG. 10 is a cross-sectional view of a chamber within a microfluidic device with a support film coated with a reagent layer, wherein the reagent layer is dimensioned to fit within the chamber, and wherein the support film seals an opening to the chamber, and the reagent layer is positioned within the chamber.

In FIG. 8, an alternative support film coated with a reagent layer 300 is illustrated, wherein the reagent layer 310 does not cover an entire major surface of support film 320. The reagent layer 310 can be coated onto support film 320 by spot coating as described herein to provide a pre-determined amount of at least one reagent in reagent layer 310, which is dimensioned to fit within a chamber, such as the chamber 50 in FIGS. 2, 3, and 4, or the chamber 55 in FIG. 10. The support film coated with the reagent layer 300 is illustrated with the support film 320 in the shape of a square or rectangle and the reagent layer 310 in the shape of a circular disc. However, other shapes can be used for support layer 320 and reagent layer 310. The reagent layer 310 covers a portion of one major surface of support film 320. The support film coated with the reagent layer 300, illustrated with one reagent layer 310, can be dimensioned to fit within a chamber 50 shown in FIGS. 2, 3, and 4 by dimensioning the support layer 320. The resulting dimensioned support film coated with the reagent layer 300 can be placed in a chamber in a manner analogous to that shown in FIGS. 2, 3, and 4. Alternatively, the support film coated with the reagent layer 300 can be placed over an opening to a chamber 55 as shown in FIG. 10, with the dimensioned reagent layer 310 within the chamber 55. In such embodiments, preferably the support film 320 is dimensioned to overlap the opening to chamber 55 and contact the substrate 20 as shown in FIG. 10. For certain of these embodiments, the support film 320 seals the opening. In FIG. 10, the opening, in which dimensioned reagent layer 310 is placed, as illustrated is dimensioned smaller than the remaining portion of the chamber 55. However, the opening can be the same dimension as the chamber, or even be dimensioned larger than the chamber.

In an alternative support film coated with a reagent layer 300, support film 320 can comprise an area large enough to include a plurality of reagent layers 310, each dimensioned to fit within a chamber. For example, support film 320 can be spot coated at a plurality of locations on support film 320 to provide an array of reagent layers 310 on support film 320. The array of reagent layers 310 on support film 320 can be combined with an array of chambers 55, one of which is shown in FIG. 10, to provide a reagent layer 310 or a plurality of reagent layers 310 in each chamber 55. Where there is a plurality of reagent layers 310, each can contain a different reagent or different combination of reagents.

A dimensioned support film coated with the reagent layer can also be provided from the array for use in a chamber as described above by cutting the support film 320 around a reagent layer 310 and placing the resulting dimensioned support film coated with the reagent layer in the chamber.

Figure 9:
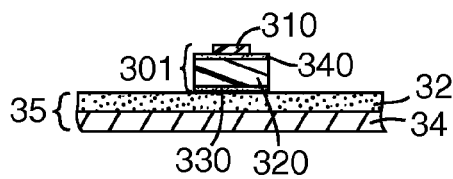
FIG. 9 is a cross-sectional view of a dimensioned support film coated with a reagent layer adhered to a sheet, wherein the reagent layer covers a portion of the support film.

Alternatively, a dimensioned support film coated with the reagent layer 301 can be adhered to a sheet as illustrated in FIG. 9, wherein either optional adhesive layer 330, optional layer 32, or both adhere dimensioned support film coated with the reagent layer 301 to sheet 35. The sheet 35 and layers 32 and 34 can be as described above. The optional adhesive layer 330 can be as described above for the optional adhesive layer 130. A plurality of the dimensioned support films coated with the reagent layer 301 can be adhered to sheet 35 and each positioned to fit within a chamber 50 when sheet 35 is used for the first layer 30 or the second layer 40 of device 10 as shown, for example, in FIG. 4.

As mentioned above, in the illustrated device of FIG. 10, the dimensioned support film coated with the reagent layer as described in FIG. 8 is placed over an opening to a chamber 55 with the reagent layer 310 within the chamber 55. The support film 320 is dimensioned to overlap the opening to chamber 55 and contact the substrate 20. An optional protective sheet 350 can be used to cover the otherwise exposed surface of support film 320 to prevent loosening of the seal between support film 320 and substrate 20. Protective sheet 350 can be bonded or attached to substrate 350 and optionally to support film 320 by, for example, a pressure sensitive adhesive, hot melt adhesive, thermoset adhesive, or a thermal bond. Protective sheet 350 can be the same as sheet 35 in FIGS. 6 and 9, for example, a polymeric film with a pressure sensitive adhesive layer. Layer 42, optional layer 44, and channel 60 are as defined for FIG. 4.

Optional adhesive layer 340 in FIGS. 8, 9, and 10 can be a pressure sensitive adhesive. When adhesive layer 340 is present, support film 320 can be a metallic sheet, for example, an aluminum foil.

For certain embodiments, including any one of the above embodiments where placing the support film coated with the reagent layer or the reagent layer portion of the support film coated with the reagent layer within the at least one chamber is included, the support film coated with the reagent layer is placed within the at least one chamber by contacting the support film coated with the reagent layer with the tip of a tube, moving the support film coated with the reagent layer held at the tip of the tube to the at least one chamber, and positioning the support film coated with the reagent layer or the reagent layer portion of the support film coated with the reagent layer within the at least one chamber. For certain of these embodiments, the support film coated with the reagent layer is preferably dimensioned. The tip of the tube may have a smaller area than a major surface of the support film coated with the reagent layer. The support film coated with the reagent layer may be held at the tip of the tube by, for example, an electrostatic charge, a pressure sensitive adhesive, or a vacuum supplied by the tube (vacuum pick-up). The tube may be a pipette, for example, a plastic pipette. The support film coated with the reagent layer is positioned within the at least one chamber so as to allow complete coverage of the reagent layer by a fluid when supplied to the at least one chamber. The support film coated with the reagent layer may be released from the tip of the tube by, for example, reducing the electrostatic charge, by attraction to an electrostatic charge within the chamber, contact with a pressure sensitive adhesive within the chamber, by contact of a pressure sensitive adhesive on the support film with a surface of the chamber, by reducing or eliminating the vacuum supplied by the tube, or by applying a positive gas pressure through the tube.

Alternatively, the support film coated with the reagent layer can be placed within the at least one chamber by punching a dimensioned support film coated with the reagent layer out of a larger support film coated with the reagent layer and allowing the dimensioned support film coated with the reagent layer to drop into the at least one chamber. In another alternative, the dimensioned support film coated with the reagent layer can be directed into the at least one chamber by the punch, a gas stream, or the like.

A pick-and-place system may be used for placing the support film coated with the reagent layer or the reagent layer portion of the support film coated with the reagent layer within the at least one chamber. The dimensioned support film coated with the reagent layer can be selected based upon the reagent(s) in the reagent layer, and a vacuum pick-up can be used to pick up and place the selected dimensioned support film coated with the reagent layer in a selected chamber, with the chamber selected based upon the action which will occur in the chamber. Additional pick-and-place methods which may be used are described in co-pending U.S. Ser. No. 60/985,827.

The chamber can permit mixing with a fluid to more rapidly dissolve, disperse, or suspend the reagent(s) in the reagent layer in the fluid. For example, the chamber can be in fluid communication with a second chamber containing a gas, such as air. When fluid is forced into the second chamber the gas is compressed, forcing at least a portion of the fluid out of the second chamber. See International Publication No. WO 2005/061084 A1 (Bedingham et al.) This fluid motion, which can be repeated numerous times, results in mixing. In another example, fluid in the chamber can be heated, causing convection currents in the fluid which brings about mixing. In another example, fluid in the chamber can be subjected to a g-force, causing a rotational motion in the fluid which brings about mixing.

For certain embodiments, including any one of the above embodiments of a method where placing the support film coated with the reagent layer within the at least one chamber is included, or including any one of the above embodiments of a device where the support film coated with the reagent layer is contained within at least one chamber of the device, the method further comprises adhering the dimensioned support film coated with the reagent layer to a surface of the at least one chamber, or for the device, the support film coated with the reagent layer is adhered to a surface of the at least one chamber. In such embodiments, the major surface of the support film, which is not coated with the reagent layer, can be adhered to a surface of the at least one chamber. A pressure sensitive adhesive, hot melt adhesive, thermoset adhesive, thermal bonding, static charge, or other like means can be used to adhere the support film to a surface of the at least one chamber. As a result, the dimensioned support film coated with the reagent layer can be held in place within the chamber, such that the reagent layer can be readily accessed for deployment of a reagent. The means for adhering the support film can be selected based upon the anticipated conditions for deploying and using the reagent. For example, a pressure sensitive adhesive can be selected, which is effective in the presence of an aqueous environment. A surface of the at least one chamber includes any surface within the chamber, including the walls, the bottom, or the top of the inside of the chamber.

For certain embodiments, including any one of the above embodiments of a method where placing the support film coated with the reagent layer within the at least one chamber is included, the method further comprises partially sealing the at least one chamber. Partially sealing includes placing a cover film, sheet, or layer over an opening into the at least one chamber while allowing a pathway for moving a fluid into the at least one chamber. The pathway can, for example, be a channel connected to the at least one chamber or be formed by piercing the cover film, sheet, or layer with a pipette or other dispensing means. Partially sealing can equip the at least one chamber so that a fluid directed into the chamber can contact the entire surface of the reagent layer of the dimensioned support film coated with the reagent layer.

For certain alternative embodiments, including any one of the above embodiments of a method where placing the support film coated with the reagent layer within the at least one chamber is included, except for embodiments where the placing is conducted in another way, the dimensioned support film coated with the reagent layer is placed within the at least one chamber by 1) adhering the dimensioned support film coated with the reagent layer to a first sheet, 2) positioning the dimensioned support film coated with the reagent layer within the at least one chamber, wherein the at least one chamber is at a first major surface of a substrate, and 3) laminating the first sheet to the first major surface of the substrate. For certain of these embodiments, the at least one chamber at the first major surface of the substrate extends through the substrate to a second major surface of the substrate. For certain of these embodiments, the method further comprises laminating a second sheet to the second major surface of the substrate. This can partially seal the at least one chamber as described above. The sheet can be a polymeric film, for example, as described for the support film, a metal sheet, or the like. The sheet can include an adhesive layer.

For certain alternative embodiments, including any one of the above embodiments of a method where placing the support film coated with the reagent layer within the at least one chamber is included, except for embodiments where the placing is conducted in another way, the reagent layer portion of the support film coated with the reagent layer is dimensioned to fit within and is placed within the at least one chamber of the device for processing sample material. For certain of these embodiments, the at least one chamber of the device for processing sample material includes an opening to the chamber, and wherein the support film coated with the reagent layer is placed over the opening with the dimensioned reagent layer within the at least one chamber. For certain of these embodiments, the support film overlaps the opening. For certain of these embodiments, the support film seals the opening.

For certain embodiments, including any one of the above embodiments where placing the support film coated with the reagent layer within the at least one chamber is included, the step of nucleic acid amplification is conducted in the at least one chamber, and wherein the reagent layer includes a nucleic acid amplifying enzyme.

For certain embodiments, including any one of the above embodiments where placing the support film coated with the reagent layer within the at least one chamber is included, the fluid which dissolves, disperses, or suspends the at least one reagent in the dry reagent layer comprises water and at least one nucleic acid.

For certain embodiments, including any one of the above embodiments where placing the support film coated with the reagent layer within the at least one chamber is included, the at least one chamber is within a microfluidic device.

For certain embodiment, including any one of the above embodiments which includes a reagent layer, preferably the reagent layer is a dry reagent layer. For certain embodiments, preferably the dry reagent layer contains not more than 50% by weight water, based upon the total weight of the dry reagent layer. For certain embodiments, the dry reagent layer contains not more than 10%, 5%, or 1% by weight water. For certain embodiments, the dry reagent layer contains not more than 1% water. For certain embodiments, the dry reagent layer contains 0% water. After the reagent layer is coated onto the support film, the reagent layer can be dried to a constant weight. For example, the coated reagent layer can be dried for a time sufficient for the weight of the coated reagent layer to remain essentially unchanged when subjected to the drying conditions for an additional period of time, thereby resulting a dry reagent layer.

For certain embodiments, including any one of the above embodiments where the support film coated with the reagent layer is present or provided, the support film coated with the reagent layer is dimensioned to fit within the at least one chamber as described supra.

The adhesive layer or the pressure sensitive adhesive mentioned in various places above can be selected to be capable of withstanding the forces generated during processing of any sample material and/or fluid in a chambers, e.g., forces developed during distributing, mixing, thermal processing, etc. of the sample material and/or fluid. The adhesive preferably exhibits low fluorescence and is compatible with the processes and materials described above.

Adhesives that exhibit pressure sensitive properties may be preferred in some circumstances. Such adhesives may be more amenable to high volume production of support films coated with reagent layers and sample processing devices since they typically do not involve the high temperature bonding processes used in melt bonding, nor do they present the handling problems inherent in use of liquid adhesives, solvent bonding, ultrasonic bonding, and the like.

One well known technique for identifying pressure sensitive adhesives is the Dahlquist criterion. This criterion defines a pressure sensitive adhesive as an adhesive having a 1 second creep compliance of greater than $1 \times 10^{-6}$ cm$^2$/dyne as described in *Handbook of Pressure Sensitive Adhesive Technology*, Donatas Satas (Ed.), $2^{nd}$ Edition, p. 172, Van Nostrand Reinhold, New York, N.Y., 1989. Alternatively, since modulus is, to a first approximation, the inverse of creep compliance, pressure sensitive adhesives may be defined as adhesives having a Young's modulus of less than $1 \times 10^6$ dynes/cm$^2$. Another well known method of identifying a pressure sensitive adhesive is that it is aggressively and permanently tacky at room temperature and firmly adheres to a variety of dissimilar surfaces upon mere contact without the need of more than finger or hand pressure, and which may be removed from smooth surfaces without leaving a residue as described in *Test Methods for Pressure Sensitive Adhesive Tapes*, Pressure Sensitive Tape Council, (1996). Another suitable definition of a suitable pressure sensitive adhesive is that it preferably has a room temperature storage modulus within the area defined by the following points as plotted on a graph of modulus versus frequency at 25° C.: a range of moduli from approximately $2 \times 10^5$ to $4 \times 10^5$ dynes/cm$^2$ at a frequency of approximately 0.1 radian/second (0.017 Hz), and a range of moduli from approximately $2 \times 10^6$ to $8 \times 10^6$ dynes/cm$^2$ at a frequency of approximately 100 radians/second (17 Hz) (for example see FIG. 8-16 on p. 173 of *Handbook of Pressure Sensitive Adhesive Technology*, Donatas Satas (Ed.), $2^{nd}$ Edition, Van Nostrand Rheinhold, New York, 1989). Any of these methods of identifying a pressure sensitive adhesive may be used to help identify potentially suitable pressure sensitive adhesives for use in the methods of the present invention.

It may be preferred that the pressure sensitive adhesives used in connection with the support films coated with reagent layers and sample processing devices of the present invention include materials which ensure that the properties of the adhesive are not adversely affected by water. For example, the pressure sensitive adhesive will preferably not lose adhesion, lose cohesive strength, soften, swell, or opacify in response to exposure to water. Also, the pressure sensitive adhesive should not contain any components which may be extracted into water during sample processing, thus possibly compromising the function of the reagent(s).

In view of these considerations, it may be preferred that the pressure sensitive adhesive be composed of hydrophobic materials. As such, it may be preferred that the pressure sensitive adhesive be composed of silicone materials. That is, the pressure sensitive adhesive may be selected from the class of silicone pressure sensitive adhesive materials, based on the combination of silicone polymers and tackifying resins, as described in, for example, "Silicone Pressure Sensitive Adhesives", *Handbook of Pressure Sensitive Adhesive Technology*, 3$^{rd}$ Edition, pp. 508-517. Silicone pressure sensitive adhesives are known for their hydrophobicity, their ability to withstand high temperatures, and their ability to bond to a variety of dissimilar surfaces.

The composition of the pressure sensitive adhesives is preferably chosen to meet the stringent requirements of the present invention. Some suitable compositions may be described in International Publication WO 00/68336 titled SILICONE ADHESIVES, ARTICLES, AND METHODS (Ko et al.).

Other suitable compositions may be based on the family of silicone-polyurea based pressure sensitive adhesives. Such compositions are described in U.S. Pat. No. 5,461,134 (Leir et al.); U.S. Pat. No. 6,007,914 (Joseph et al.); International Publication No. WO 96/35458 (and its related U.S. patent application Ser. No. 08/427,788 (filed Apr. 25, 1995); Ser. No. 08/428,934 (filed Apr. 25, 1995); Ser. No. 08/588,157 (filed Jan. 17, 1996); and Ser. No. 08/588,159 (filed Jan. 17, 1996); International Publication No. WO 96/34028 (and its related U.S. patent application Ser. No. 08/428,299 (filed Apr. 25, 1995); Ser. No. 08/428,936 (filed Apr. 25, 1995); Ser. No. 08/569,909 (filed Dec. 8, 1995); and Ser. No. 08/569,877 (filed Dec. 8, 1995)); and International Publication No. WO 96/34029 (and its related U.S. patent application Ser. No. 08/428,735 (filed Apr. 25, 1995) and Ser. No. 08/591,205 (filed Jan. 17, 1996)).

Such pressure sensitive adhesives are based on the combination of silicone-polyurea polymers and tackifying agents. Tackifying agents can be chosen from within the categories of functional (reactive) and nonfunctional tackifiers as desired. The level of tackifying agent or agents can be varied as desired so as to impart the desired tackiness to the adhesive composition. For example, it may be preferred that the pressure sensitive adhesive composition be a tackified polydiorganosiloxane oligurea segmented copolymer including (a) soft polydiorganosiloxane units, hard polyisocyanate residue units, wherein the polyisocyanate residue is the polyisocyanate minus the —NCO groups, optionally, soft and/or hard organic polyamine units, wherein the residues of isocyanate units and amine units are connected by urea linkages; and (b) one or more tackifying agents (e.g., silicate resins, etc.).

Furthermore, the adhesive layer or pressure sensitive adhesive used with the support films coated with reagent layers and sample processing devices of the present invention can be a single pressure sensitive adhesive or a combination or blend of two or more pressure sensitive adhesives. The pressure sensitive layers may result from solvent coating, screen printing, roller printing, melt extrusion coating, melt spraying, stripe coating, or laminating processes, for example. An adhesive layer can have a wide variety of thicknesses as long as it meets exhibits the above characteristics and properties. The adhesive layer may be continuous and free from pinholes or porosity, for example, when serving as a passivation layer.

It is to be understood that in any of the embodiments described herein where a support film coated with a reagent layer or the reagent layer portion of the support film coated with the reagent layer is placed within or contained within a chamber, one or a plurality of support films coated with the reagent layer or a plurality of the reagent layer portions of the support films are placed or contained within the chamber. Each reagent layer can be separated by a space from any other reagent layer that is present. Each reagent layer that is present can contain a different reagent or a different combination of reagents. The spatial separation of reagents can provide increase stability during processing, such as during drying and storage of reagents. For example, separation of a polymerase enzyme from primers can prevent primer dimer formation and other undesirable reactions from occurring. In addition, spatial separation of reagents can result in faster re-suspension of each reagent. Moreover, spatial separation of reagents can allow control over the order in which the reagents are re-suspended and combined.

LIST OF EMBODIMENTS

The following is a listing of some of the embodiments described above, where "emb" means "embodiment" and "embs" means "embodiments".

1. A method of providing at least one reagent for processing sample material, the method comprising:
    providing a support film coated with a reagent layer which includes the at least one reagent; and
    dimensioning the reagent layer or the reagent layer and support film to fit within at least one chamber of a device for processing sample material, wherein the at least one chamber can contain or channel a fluid.
2. The method of emb 1, further comprising adhering the dimensioned support film coated with the reagent layer to a sheet.
3. A method of delivering at least one reagent to a device for processing sample material, the method comprising:
    providing a support film coated with a reagent layer which includes the at least one reagent;
    placing the support film coated with the reagent layer or the reagent layer portion of the support film coated with the reagent layer within at least one chamber of a device for processing sample material, wherein the at least one chamber can contain or channel a fluid; and wherein the reagent layer or the reagent layer and support film are dimensioned to fit within the at least one chamber of the device for processing sample material.
4. The method of emb 3 further comprising dimensioning the reagent layer or the reagent layer and support film to fit within the at least one chamber of the device for processing sample material.
5. The method of any one of embs 1 through 4 wherein the at least one reagent can be used in at least one of a step of sample preparation, a step of nucleic acid amplification, and a step of detection in a process for detecting or assaying a nucleic acid.
6. The method of emb 5, wherein the at least one reagent is selected from the group consisting of a lysis reagent, a protein-digesting reagent, a nucleic acid amplifying enzyme, an oligonucleotide, a probe, nucleotide triphosphates, a buffer, a salt, a surfactant, a dye, a nucleic acid control, a reducing agent, dimethyl sulfoxide (DMSO), glycerol, ethylenediaminetetraacetic acid (EDTA), ethylene glycol-bis(2-aminoethylether)-N,N,N',N'-tetraacetic acid (EGTA), microspheres capable of binding a nucleic acid, and a combination thereof.
7. The method of emb 6, wherein the at least one reagent is selected from the group consisting of a nucleic acid amplifying enzyme, a primer, and a probe.
8. The method of emb 7, wherein the at least one reagent is a nucleic acid amplifying enzyme.

9. The method of any one of embs 1 through 8, wherein the reagent layer further includes a matrix material selected from the group consisting of a water soluble polymer, a carbohydrate, and a combination thereof.

10. The method of emb 9, wherein the matrix material is a water soluble polymer.

11. The method of emb 9, wherein the matrix material is a carbohydrate.

12. The method of emb 9 wherein the matrix material is a combination of a water soluble polymer and a carbohydrate.

13. The method of any one of embs 9, 10, and 12, wherein the water soluble polymer is selected from the group consisting of poly(vinyl alcohol), poly(vinyl alcohol acetate), polyvinylpyrrolidone, and a combination thereof.

14. The method of any one of embs 9, 11, 12, or emb 13 as dependent on emb 12, wherein the carbohydrate is selected from the group consisting of sucrose, dextran, trehalose, pullulan, α-cyclodextrin, mannitol, sorbitol, and a combination thereof.

15. The method of any one of embs 1 through 14, wherein the support film is substantially insoluble in water.

16. The method of any one of embs 1 through 15, wherein the support film coated with the reagent layer has a thickness of not more than 250µ, and wherein the thickness includes both the support film and the reagent layer.

17. The method of emb 16, wherein the reagent layer has a thickness of not more than 25µ.

18. The method of any one of embs 1 through 17, wherein the support film coated with the reagent layer is further dimensioned to provide a pre-determined amount of the at least one reagent.

19. The method of any one of embs 1 through 18, wherein the device for processing sample material is a microfluidic device.

20. The method of any one of embs 3, 4, and 5 through 19 except as dependent on emb 1 or claim 2, wherein the dimensioned support film coated with the reagent layer is placed within the at least one chamber by contacting the dimensioned support film coated with the reagent layer with the tip of a tube, moving the dimensioned support film coated with the reagent layer held at the tip of the tube to the at least one chamber, and positioning the dimensioned support film coated with the reagent layer within the at least one chamber.

21. The method of any one of embs 3, 4, 5 through 19 except as dependent on emb 1 or emb 2, and emb 20, further comprising adhering the dimensioned support film coated with the reagent layer is to a surface of the at least one chamber.

22. The method of any one of embs 3, 4, 5 through 19 except as dependent on emb 1 or emb 2, 20, and 21, further comprising partially sealing the at least one chamber.

23. The method of any one of embs 3, 4, and 5 through 19 except as dependent on emb 1 or emb 2, wherein the dimensioned support film coated with the reagent layer is placed within the at least one chamber by 1) adhering the dimensioned support film coated with the reagent layer to a first sheet, 2) positioning the dimensioned support film coated with the reagent layer within the at least one chamber, wherein the at least one chamber is at a first major surface of a substrate, and 3) laminating the first sheet to the first major surface of the substrate.

24. The method of emb 23 wherein the at least one chamber extends through the substrate to a second major surface of the substrate.

25. The method of emb 24, further comprising laminating a second sheet to the second major surface of the substrate.

26. The method of any one of embs 3, 4, and 5 through 19 except as dependent on emb 1 or emb 2, wherein the reagent layer portion of the support film coated with the reagent layer is dimensioned to fit within and is placed within the at least one chamber of the device for processing sample material.

27. The method of emb 26, wherein the at least one chamber of the device for processing sample material includes an opening to the chamber, and wherein the support film coated with the reagent layer is placed over the opening with the dimensioned reagent layer within the at least one chamber.

28. The method of emb 27, wherein the support film overlaps the opening.

29. The method of emb 28, wherein the support film seals the opening.

30. A method of adding at least one reagent to at least one step in a process for detecting or assaying a nucleic acid, the method comprising:
providing a support film coated with a dry reagent layer which includes the at least one reagent;
placing the support film coated with the dry reagent layer or the dry reagent layer portion of the support film coated with the dry reagent layer in at least one chamber which can contain or channel a fluid, wherein the at least one step is conducted in the at least one chamber, and wherein the at least one step is selected from the group consisting of sample preparation, nucleic acid amplification, and detection; and
contacting the dry reagent layer with a fluid which dissolves, disperses, or suspends the at least one reagent in the reagent layer.

31. The method of emb 30, wherein the at least one reagent is used in at least one of a step of sample preparation, a step of nucleic acid amplification, and a step of detection in a process for detecting or assaying a nucleic acid.

32. The method of emb 31, wherein the at least one reagent is selected from the group consisting of a lysis reagent, a protein-digesting reagent, a nucleic acid amplifying enzyme, an oligonucleotide, a probe, nucleotide triphosphates, a buffer, a salt, a surfactant, a dye, a nucleic acid control, a reducing agent, dimethyl sulfoxide (DMSO), glycerol, ethylenediaminetetraacetic acid (EDTA), ethylene glycol-bis(2-aminoethylether)-N,N,N',N'-tetraacetic acid (EGTA), microspheres capable of binding a nucleic acid, and a combination thereof.

33. The method of emb 32, wherein the at least one reagent is selected from the group consisting of a nucleic acid amplifying enzyme, a primer, and a probe.

34. The method of emb 33, wherein the at least one reagent is a nucleic acid amplifying enzyme.

35. The method of any one of embs 30 through 34, wherein the dry reagent layer further includes a matrix material selected from the group consisting of a water soluble polymer, a carbohydrate, and a combination thereof.

36. The method of emb 35, wherein the matrix material is a water soluble polymer.

37. The method of 35, wherein the matrix material is a carbohydrate.

38. The method of emb 52 wherein the matrix material is a combination of a water soluble polymer and a carbohydrate.

39. The method of any one of embs 35, 36, and 38, wherein the water soluble polymer is selected from the group consisting of poly(vinyl alcohol), poly(vinyl alcohol acetate), polyvinylpyrrolidone, and a combination thereof.

40. The method of any one of embs 35, 37, 38, or emb 39 as dependent on emb 38, wherein the carbohydrate is selected from the group consisting of sucrose, dextran, trehalose, pullulan, α-cyclodextrin, mannitol, sorbitol, and a combination thereof.

41. The method of any one of embs 30 through 40, wherein the support film is substantially insoluble in water.

42. The method of any one of embs 30 through 41, wherein the support film coated with the dry reagent layer has a thickness of not more than 250μ, and wherein the thickness includes both the support film and the reagent layer.

43. The method of emb 42, wherein the dry reagent layer has a thickness of not more than 25μ.

44. The method of any one of embs 30 through 43, wherein the support film coated with the dry reagent layer is placed within the at least one chamber by contacting the support film coated with the dry reagent layer with the tip of a tube, moving the support film coated with the dry reagent layer held at the tip of the tube to the at least one chamber, and positioning the support film coated with the dry reagent layer within the at least one chamber.

45. The method of any one of embs 30 through 44, further comprising adhering the dimensioned support film coated with the dry reagent layer is to a surface of the at least one chamber.

46. The method of any one of embs 30 through 45, further comprising partially sealing the at least one chamber.

47. The method of any one of embs 30 through 43, wherein the dimensioned support film coated with the dry reagent layer is placed within the at least one chamber by 1) adhering the dimensioned support film coated with the dry reagent layer to a first sheet, 2) positioning the dimensioned support film coated with the dry reagent layer within the at least one chamber, at an opening to the at least one chamber, wherein the opening is at a first major surface of a substrate, and 3) laminating the first sheet to the first major surface of the substrate.

48. The method of emb 47 wherein the at least one chamber extends through the substrate to a second major surface of the substrate.

49. The method of emb 48, further comprising laminating a second sheet to the second major surface of the substrate.

50. The method of any one of embs 30 through 43, wherein the reagent layer portion of the support film coated with the reagent layer is dimensioned to fit within and is placed within the at least one chamber of the device for processing sample material.

51. The method of emb 50, wherein the at least one chamber of the device for processing sample material includes an opening to the chamber, and wherein the support film coated with the reagent layer is placed over the opening with the dimensioned reagent layer within the at least one chamber.

52. The method of emb 51, wherein the support film overlaps the opening.

53. The method of emb 52, wherein the support film seals the opening.

54. The method of any one of embs 30 through 53, wherein the step of nucleic acid amplification is conducted in the at least one chamber, and wherein the dry reagent layer includes a nucleic acid amplifying enzyme.

55. The method of any one of embs 30 through 54, wherein the fluid which dissolves, disperses, or suspends the at least one reagent in the dry reagent layer comprises water and at least one nucleic acid.

56. The method of any one of embs 30 through 55, wherein the at least one chamber capable of containing or channeling the fluid is within a microfluidic device.

57. A support film coated with a dry reagent layer, wherein the reagent layer or the reagent layer and support film are dimensioned to fit within at least one chamber of a microfluidic device.

58. A support film coated with a dry reagent layer, wherein the dry reagent layer comprises at least one reagent which can be used in at least one of a step of sample preparation, a step of nucleic acid amplification, and a step of detection in a process for detecting or assaying a nucleic acid.

59. The support film coated with the dry reagent layer of emb 58, wherein the dry reagent layer or the dry reagent layer and support film are dimensioned to fit within a chamber capable of containing or channeling a fluid within a microfluidic device.

60. The support film coated with the dry reagent layer of emb 57 or emb 59, wherein the dimensioned support film coated with the dry reagent layer is adhered to a sheet.

61. The support film coated with the dry reagent layer of emb 60, wherein a plurality of the dimensioned support films coated with the dry reagent layer are adhered to the sheet.

62. The support film coated with the dry reagent layer of emb 59, wherein the support film coated with the dry reagent layer comprises an area of at least about 1 mm² and not more than about 50 mm²

63. The support film coated with the dry reagent layer of any one of embs 57 through 62, wherein the dry reagent layer comprises at least one reagent selected from the group consisting of a lysis reagent, a protein-digesting reagent, a nucleic acid amplifying enzyme, an oligonucleotide, a probe, nucleotide triphosphates, a buffer, a salt, a surfactant, a dye, a nucleic acid control, a reducing agent, dimethyl sulfoxide (DMSO), glycerol, ethylenediaminetetraacetic acid (EDTA), ethylene glycol-bis(2-aminoethylether)-N,N,N',N'-tetraacetic acid (EGTA), microspheres capable of binding a nucleic acid, and a combination thereof.

64. The support film coated with the dry reagent layer of emb 63, wherein the dry reagent layer includes a nucleic acid amplifying enzyme.

65. The support film coated with the dry reagent layer of any one of embs 57 through 64, wherein the dry reagent layer further includes a matrix material selected from the group consisting of a water soluble polymer, a carbohydrate, and a combination thereof.

66. The support film coated with the dry reagent layer of any one of embs 57 through 65, wherein the support film is substantially insoluble in water.

67. The support film coated with the dry reagent layer of any one of embs 57 through 66, wherein the support film coated with the dry reagent layer has a thickness of not more than 250μ, and wherein the thickness includes both the support film and the reagent layer.

68. The support film coated with the dry reagent layer of emb 67, wherein the reagent layer has a thickness of not more than 25μ.

69. The support film coated with the dry reagent layer of any one of embs 57 through 68, wherein the support film coated with the dry reagent layer is dimensioned to provide a predetermined amount of the at least one reagent.

70. A device for processing sample material, the device having a plurality of chambers which can contain or channel a fluid, wherein a support film coated with a dry reagent layer or the dry reagent layer portion of the support film coated with the dry reagent layer is dimensioned to fit within and is contained within at least one chamber of the device.

71. The device of emb 70, wherein the dry reagent layer includes at least one reagent which can be used in at least one of a step of sample preparation, a step of nucleic acid amplification, and a step of detection in a process for detecting or assaying a nucleic acid.

72. The device of emb 71, wherein the dry reagent layer includes at least one reagent selected from the group consisting of a lysis reagent, a protein-digesting reagent, a nucleic acid amplifying enzyme, an oligonucleotide, a probe, nucleotide triphosphates, a buffer, a salt, a surfactant, a dye, a nucleic acid control, a reducing agent, dimethyl sulfoxide (DMSO), glycerol, ethylenediaminetetraacetic acid (EDTA), ethylene glycol-bis(2-aminoethylether)-N,N,N',N'-tetraacetic acid (EGTA), microspheres capable of binding a nucleic acid, and a combination thereof.

73. The device of emb 72, wherein the dry reagent layer includes at least one reagent selected from the group consisting of a nucleic acid amplifying enzyme, a primer, and a probe.

74. The device of emb 73, wherein the dry reagent layer includes a nucleic acid amplifying enzyme.

75. The device of any one of embs 70 through 74, wherein the dry reagent layer further includes a matrix material selected from the group consisting of a water soluble polymer, a carbohydrate, and a combination thereof.

76. The method of emb 75, wherein the matrix material is a water soluble polymer.

77. The method of emb 75, wherein the matrix material is a carbohydrate.

78. The method of emb 75 wherein the matrix material is a combination of a water soluble polymer and a carbohydrate.

79. The method of any one of embs 75, 76, and 78, wherein the water soluble polymer is selected from the group consisting of poly(vinyl alcohol), poly(vinyl alcohol acetate), polyvinylpyrrolidone, and a combination thereof.

80. The method of any one of embs 75, 77, 78, or emb 79 as dependent on emb 78, wherein the carbohydrate is selected from the group consisting of sucrose, dextran, trehalose, pullulan, α-cyclodextrin, mannitol, sorbitol, and a combination thereof.

81. The device of any one of embs 70 through 80, wherein the support film is substantially insoluble in water.

82. The device of emb 81, wherein the support film is a low-fluorescing film comprised of a polymer selected from the group consisting of a polyester, a polycarbonate, a polypropylene, a polyethylene, a poly(vinyl acetate), a poly(acrylate), a poly(methacrylate), and combinations thereof.

83. The device of emb 82, wherein the support film is comprised of an oriented polyester or polypropylene.

84. The device of any one of embs 70 through 83, wherein the support film coated with the dry reagent layer has a thickness of not more than 250μ, and wherein the thickness includes both the support film and the reagent layer.

85. The device of emb 84, wherein the dry reagent layer has a thickness of not more than 25μ.

86. The device of any one of embs 70 through 85, wherein the device is a microfluidic device.

87. The device of any one of embs 70 through 86, wherein the support film coated with the dry reagent layer is adhered to a surface of the at least one chamber.

88. The method of any one of embs 1 though 56, wherein the reagent layer is a dry reagent layer.

89. The method of any one of embs 57 through 88, wherein the dry reagent layer has a water content of not more than 1% by weight of the dry reagent layer.

Objects and advantages of this invention are further illustrated by the following examples, but the particular materials and amounts thereof recited in these examples, as well as other conditions and details, should not be construed to unduly limit this invention.

EXAMPLES

Example 1

Support Enzyme Films

A homogeneous aqueous excipient/enzyme master mixture was prepared by combining 20 μL of LightCycler® DNA Master HybProbe (Cat. No. 12158825001, Roche, Indianapolis, Ind.) and 40 μL of an aqueous solution containing 5% polyvinyl alcohol (PVA, average mw=30,000-70,000, Cat. No. p-8136, Sigma Chemical Co.) and 10% w/v sucrose (Cat#S-0389, Sigma Chemical Co.) in a 1.6 mL eppendorf tube. The already homogenous solution was vortexed, and centrifuged.

Loparex silicone release liner (Part No. 11-0021-1098-6, Loparex Inc., Iowa City, Iowa) was used as the support film for these coatings. The liner was cut into two strips measuring 12 mm×5 mm. The enzyme formulation (30 μL, enough to provide enzyme for 8 reactions) was evenly coated by hand onto the major surface of the strips not having the silicone release coating. The strips were left to air dry in a HEPA-filtered drying cabinet for 2 hours. The strips were then cut into approximately equal pieces approximately 1.5 mm wide by 5 mm high, to fit into the outer wells of a Fastman Sample Processing Device; in this case, an Open Architecture (OA) disc. (Sample processing devices referred to in the present invention may be similar to those described in, for example, U.S. Patent Application Publication Nos. 2002/0064885 (Bedingham et al.); 2002/0048533 (Bedingham et al.); 2002/0047003 (Bedingham et al.); 2003/138779 (Parthasarathy et al.); U.S. Pat. No. 6,627,159 B1 (Bedingham et al.), and International Publication No. WO 2005/061084 A1 (Bedingham et al.). These documents disclose a variety of different constructions of sample processing devices that may be used in the present invention). Cutting was performed using a razor blade on an aluminum block and transfer into the OA disc was performed by gently sticking the coated support film to the end of a plastic pipette tip followed by placement into the outer well of the OA disc by touching the liner material to the adhesive surface of the well. A total of 16 pieces were transferred to the disc. In preparation for PCR, the outer wells were then sealed by pressure laminating a polyester film with adhesive to the disc, using a Carver hydraulic press (Model No. 3889.1DI0A05, Carver, Inc., Wabash, Ind.).

Example 2

Real Time PCR (RT-PCR)

After the support films coated with the reagent layer containing the dried PCR reagents were placed into the outer wells of the spokes on the OA disc as shown in FIG. 1, and the wells sealed as describe in Example 1, the enzyme and other components on the support film was re-suspended by mixing on the disc using alternating velocities between 3000 and 0 rpm for 5 minutes. Mixing was accomplished on the disc using both wet controls (un-dried reagents and no support film) and support films coated with the reagent layer containing the dried PCR reagents. cDNA (Clontech, Mountain View, Calif.) was used with both the wet controls and the dried reagents. For the wet controls, 8 μL of the aqueous solution containing 5% polyvinyl alcohol and 10% w/v sucrose plus 2 ΞL of the LightCycler® DNA Master HybProbe were introduced into empty wells. For the dried reagents, PCR-grade $H_2O$ was introduced to the wells that contained the dried-down reagent layer containing the enzyme and other components on the support film. The $H_2O$ then re-hydrated and re-suspended the enzyme and the other reagents on the films within the wells. The contents of each well, including both wet control sets and re-hydrated dried reagents were then transferred to a LightCycler capillary, and after addition of the solution specified in Table 1, PCR was commence using the time and temperature parameters specified in Table 2. A three-log dilution series of cDNA was used to illustrate the dynamic range of the assay, ranging from 20 ng/reaction down to 0.2 ng/reaction. A 3-fold dilution series of cDNA was amplified using an assay containing h-HPRT primers and a fluorescein-labeled probe (Roche Applied Science).

To the two sets of LightCycler capillaries (one containing re-hydrated enzyme solution and the second containing the wet control enzyme solution) was added a 10 µL solution of the components shown in Table 1. RT-PCR assays were run on duplicates of three dilution points of 20, 2, and 0.2 ng of cDNA.

TABLE 1

PCR reagent list.

| Reagent | Volume (µL) |
|---|---|
| h-HPRT Detection Mix, 10x (Roche Applied Science) | 2.0 |
| 25 mM MgCl$_2$ | 4.0 |
| 20, 2, and 0.2 ng of cDNA (Clontech, Mountain View, CA) | 4.0 |

A wet control dilution series was run in the LightCycler capillaries by adding 10 µL of the above reaction mixture. In addition, two no template control (NTC) reactions were run for each of the formulations. The NTC reactions contained 4 µL of PCR grade water instead of the DNA.

After loading the above mixtures into capillaries, the thermocycle protocol was then commenced and data was collected according to the thermocycling program shown below in Table 2, and the results are shown in Table 3 below.

TABLE 2

LightCycler Thermocycling Conditions.

| Number Of Cycles | Temperature(s) Within Each Cycle (° C.) | Time (seconds) |
|---|---|---|
| 1 | 95 | 60 |
| 45 | 95 | 0 |
|  | 55 | 15* |
|  | 72 | 15 |

*Data was collected at this point in the cycle during each of the 45 cycles.

TABLE 3

Tabulated Ct Values Comparing Coated Enzyme Films With Wet Controls. Ct values are shown for replicates run under each condition.

| Enzyme Master Mix | DNA Sample (ng) | Ct Value | | | |
|---|---|---|---|---|---|
| Coated Enzyme Film | 20 | 24.7 | 24.2 | 24.5 | 24.1 |
|  | 2 | 27.5 | 27.9 | 27.8 | 27.1 |
|  | 0.2 | 29.2 | 30.2 | 29.7 | 29.8 |
| Wet Controls | 20 | 24.1 | 24.0 |  |  |
|  | 2 | 26.9 | 26.8 |  |  |
|  | 0.2 | 30.6 | 31.3 |  |  |

Example 6

Printing Compositions Containing Magnetic Microparticles

A 10 mL volume of solution containing 10 weight percent sucrose and 5 weight percent dextran in 0.2 M MES buffer (pH 5.5 with 0.1 weight percent TRITON X-100) was mixed with Brilliant Bromcresol Blue dye (5 mg) and 1 micron Ga(III)-microparticles (50 mg/mL of solution) to provide a composition for printing. The composition was printed using a BIODOT AD3200 BIOJET PLUS printer (Biodot Inc. Irvine, Calif. 92614). An array of spots was printed at 2 µL/spot on the adhesive side of a PET film coated with a tackified silicone-polyurea polymer adhesive, each spot with a diameter of about 2 mm and containing about 100 µg of magnetic microparticles. The spots were air dried overnight. All spots were uniform in size with no observable cracks or flaws.

Preparation of Ga(III)-Microparticles:

Metal-ion mediated magnetic microparticles, were prepared from magnetic particles with surface carboxylic acid groups and with a diameter of about 1 micron (µ) (SERA-MAG Magnetic Particles from Thermo Scientific (known as Seradyn, Indianapolis, Ind.), as described in U.S. Ser. No. 60/913,812. The carboxylated magnetic microparticles were placed in a tube and washed by attracting them to the wall of the tube using a magnet, removing the liquid by aspiration, replacing the liquid volume with the wash solution, removing the tube from the magnetic field, and agitating the tube to resuspend the microparticles.

Prior to metal-ion treatment, the magnetic microparticles were washed twice with 0.1 M MES buffer, pH 5.5 (containing 0.1% TRITON X-100) and then re-suspended in the same buffer. Following the wash step, 0.2 mL of 0.1 M gallium (III) nitrate in 0.01 M HCl solution per milligram of magnetic microparticles was added to the magnetic microparticle suspension. The mixture was allowed to shake gently for 1 h at room temperature and subsequently washed with the above MES buffer to remove excess metal ions. The resulting metal-ion mediated magnetic microparticles (Ga(III)-microparticles) were resuspended and stored at 4° C. in MES buffer.

All references and publications or portions thereof cited herein are expressly incorporated herein by reference in their entirety into this disclosure. Exemplary embodiments of this invention are discussed and reference has been made to some possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the embs provided below and equivalents thereof.

What is claimed is:

1. A device for processing sample material, the device having a plurality of chambers and channels configured for fluid delivery, the device further having channels between the chambers; wherein at least one chamber further comprises a substrate, a first layer, a second layer, a support film on the first layer, and an adhesive layer between the support film and the first layer; wherein the support film further comprises a dry reagent layer, or a dry reagent layer coated on a portion of the support film, and an adhesion promoting layer between the reagent layer and the support film; wherein the support film is dimensioned to fit within and is contained within at least one chamber of the device; wherein the dry reagent layer, which can be dissolved, dispersed, or suspended in an aqueous fluid, comprises at least one reagent which can be used in at least one of a step of sample preparation, a step of nucleic acid amplification, and a step of detection in a process for detecting or assaying a nucleic acid; and wherein the adhesive layer is a pressure sensitive adhesive layer.

2. The device of claim 1, wherein the dry reagent layer further includes a matrix material selected from the group consisting of a water soluble polymer, a carbohydrate, and a combination thereof; and wherein the material can be dissolved, dispersed, or suspended in water at a temperature of at least room temperature and not more than 97° C.

3. The device of claim 1, wherein the at least one reagent is selected from the group consisting of a nucleic acid amplifying enzyme, a primer, a probe, and microspheres capable of binding a nucleic acid.

4. The device of claim 3, wherein the at least one reagent is a nucleic acid amplifying enzyme.

5. The device of claim 1, wherein the device is a microfluidic device.

6. The device of claim 1, wherein the support film coated with the dry reagent layer is adhered to a surface of the at least one chamber.

7. The device of claim 1, wherein the dry reagent layer has a water content of not more than 1% by weight of the dry reagent layer.

\* \* \* \* \*

UNITED STATES PATENT AND TRADEMARK OFFICE
CERTIFICATE OF CORRECTION

PATENT NO. : 8,835,157 B2
APPLICATION NO. : 12/597410
DATED : September 16, 2014
INVENTOR(S) : Ranjani Parthasarathy et al.

Page 1 of 1

It is certified that error appears in the above-identified patent and that said Letters Patent is hereby corrected as shown below:

In the Specification

Column 4
Line 40, delete "mm²" and insert -- $mm^2$, --, therefor.

Column 6
Line 30, delete "minus" and insert -- minus. --, therefor.

Column 9
Line 57, delete "polyvinyl" and insert -- poly(vinyl --, therefor.

Column 28
Line 56, delete "  " and insert -- 2 µL --, therefor.

Signed and Sealed this
Second Day of June, 2015

Michelle K. Lee
*Director of the United States Patent and Trademark Office*